United States Patent [19]  
Feezor

[11] 4,038,496  
[45] July 26, 1977

[54] PORTABLE BEKESY TYPE DIAGNOSTIC AUDIOMETER

[75] Inventor: Michael D. Feezor, Chapel Hill, N.C.

[73] Assignee: Audiometric Teleprocessing, Inc., Chapel Hill, N.C.

[21] Appl. No.: 577,626

[22] Filed: May 15, 1975

[51] Int. Cl.² .......................................... H04R 29/00
[52] U.S. Cl. ................................................. 179/1 N
[58] Field of Search ........................................ 179/1 N

[56] References Cited

U.S. PATENT DOCUMENTS

| 2,563,384 | 8/1951 | Von Bekesy | 179/1 N |
| 3,673,328 | 6/1972 | Grason et al. | 179/1 N |
| 3,793,484 | 2/1974 | Feezor et al. | 179/1 N |
| 3,808,354 | 4/1974 | Feezor | 179/1 N |
| 3,809,811 | 5/1975 | Delisle et al. | 179/1 N |
| 3,905,131 | 9/1975 | Feezor et al. | 179/1 N |

Primary Examiner—Kathleen H. Claffy  
Assistant Examiner—E. S. Kemeny  
Attorney, Agent, or Firm—B. B. Olive

[57] ABSTRACT

A portable precision automatic audiometer for testing hearing of an individual utilizes a voltage programmable oscillator in combination with a preprogrammed logic circuit to generate and transmit sweep frequency tones automatically or fixed frequency tones under manual control into a suitable earphone worn by the individual examinee being tested. A voltage proportional attenuator is controlled by an examinee manually operated switch and enables the examinee being tested to regulate the level of sound pressure to which he is being exposed, while a chart recording instrument simultaneously graphs the audiogram of his test responses. Improvements are provided with respect to noise reduction and ease of calibration. Features of the invention include the elimination of sources of mechanical noise, the employment of a programmed logic controlled voltage source for the oscillator to provide a sweep frequency mode of operation, the employment of a noise source to mask the ear not being tested and a switching arrangement which allows the noise source to be switched from ear-to-ear in correspondence with the test procedure.

16 Claims, 23 Drawing Figures

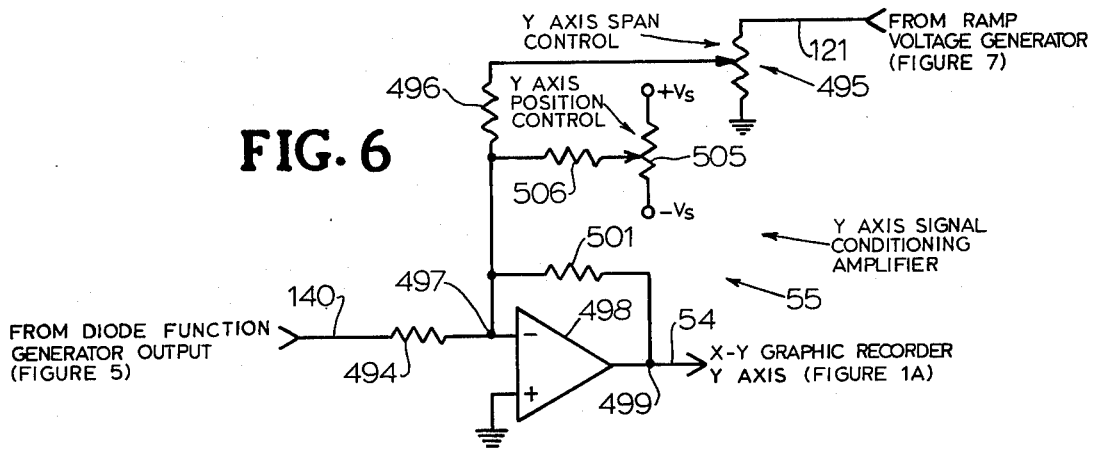
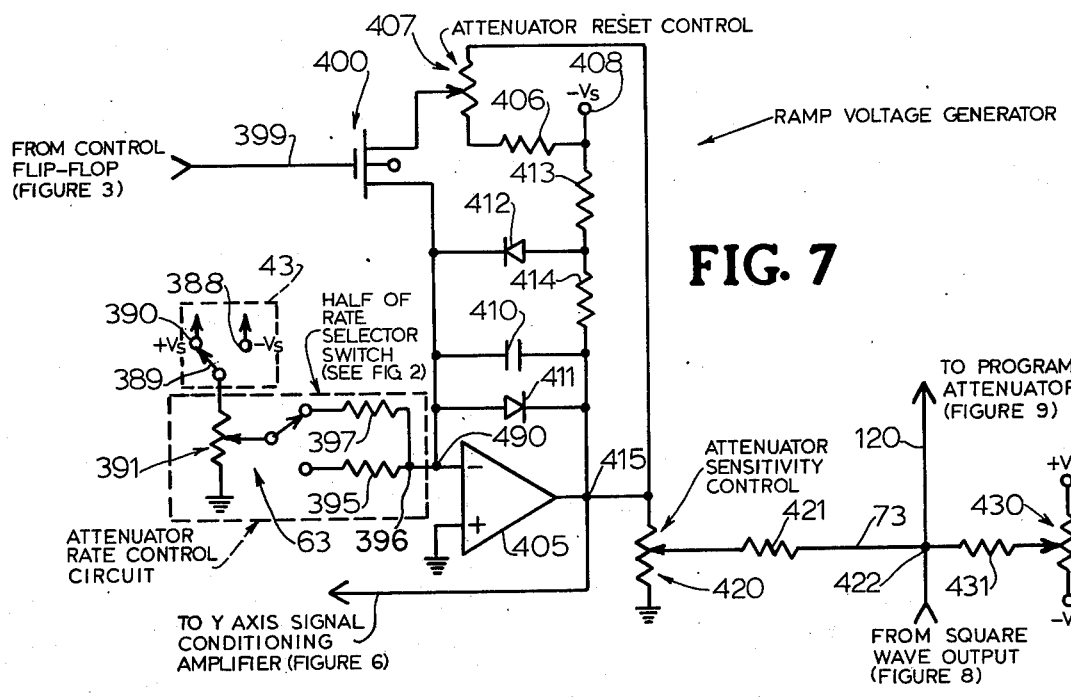
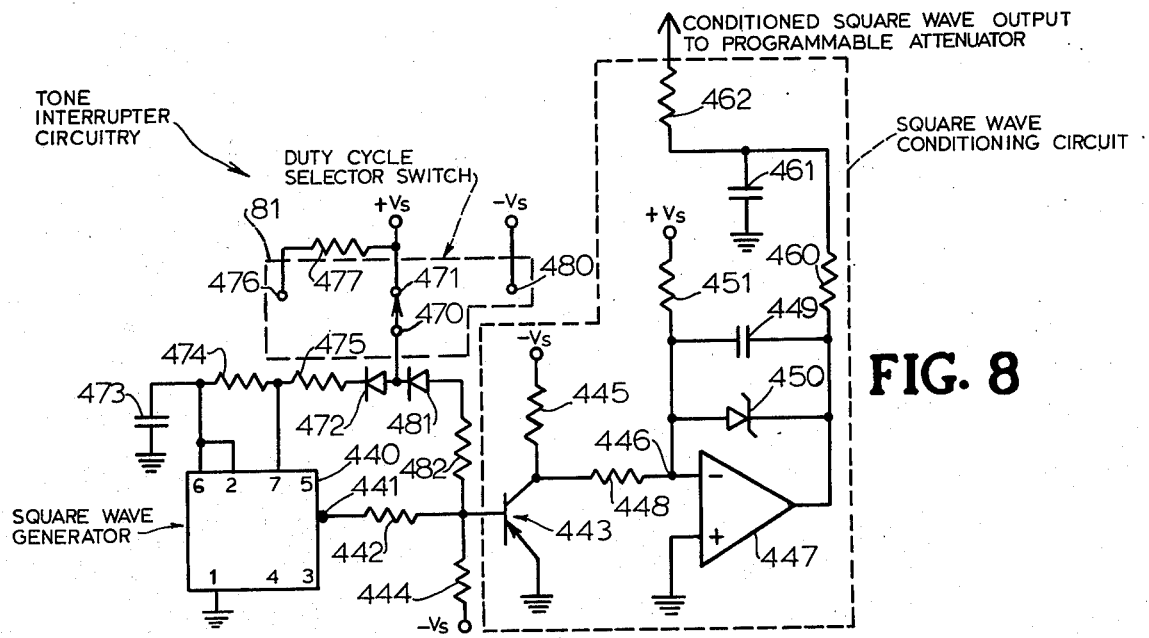

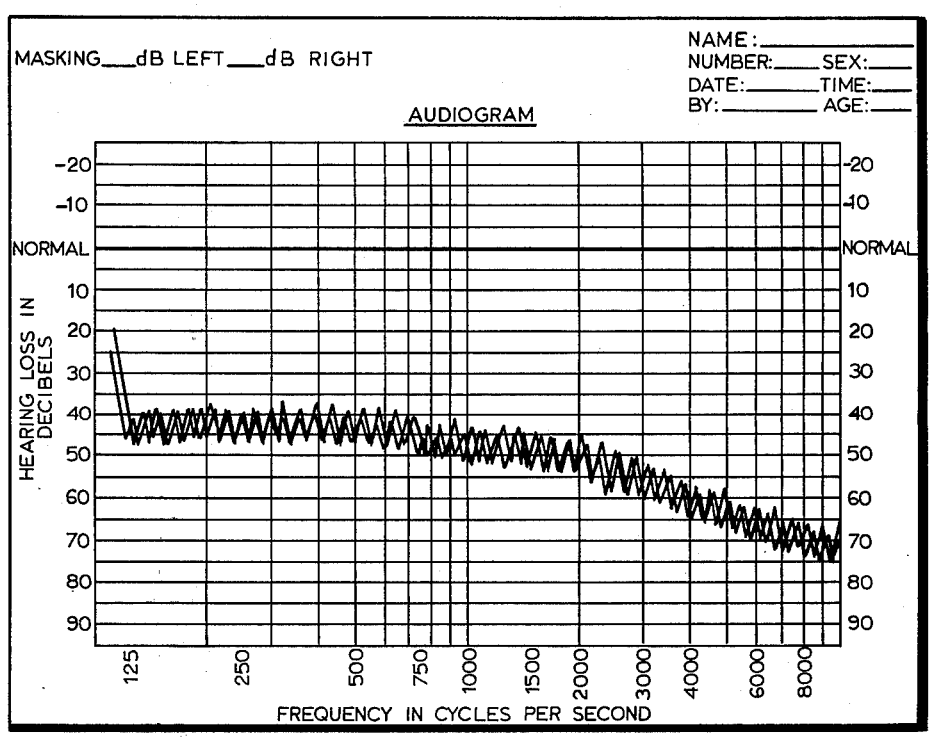
FIG. 19 (TYPE I BEKESY AUDIOGRAM)
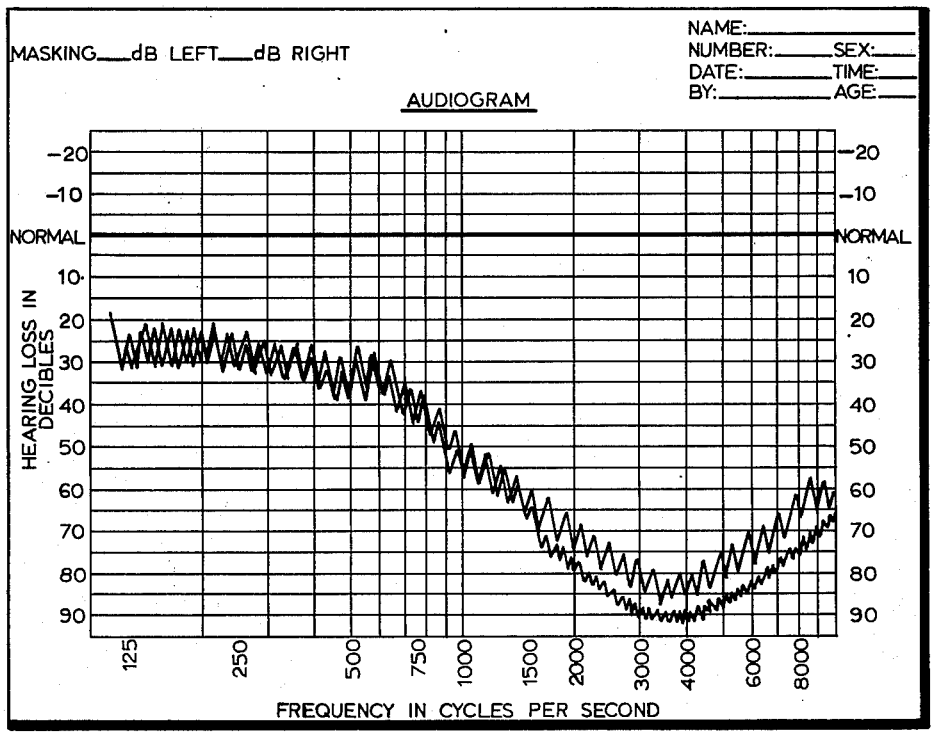
FIG. 20 (TYPE II BEKESY AUDIOGRAM)

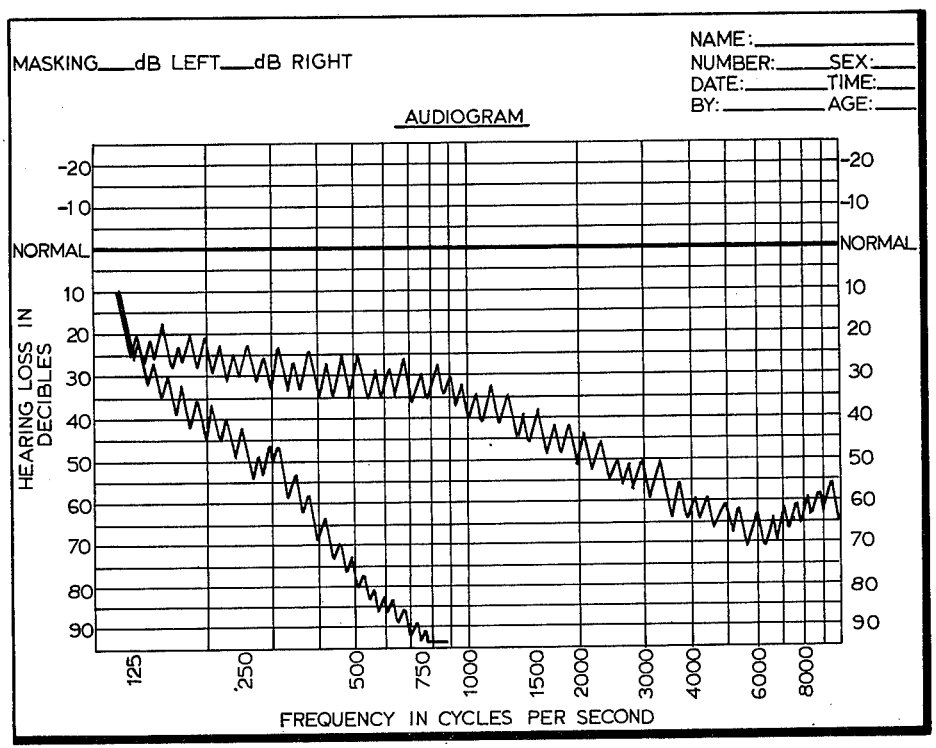
FIG. 21 (TYPE III BEKESY AUDIOGRAM)
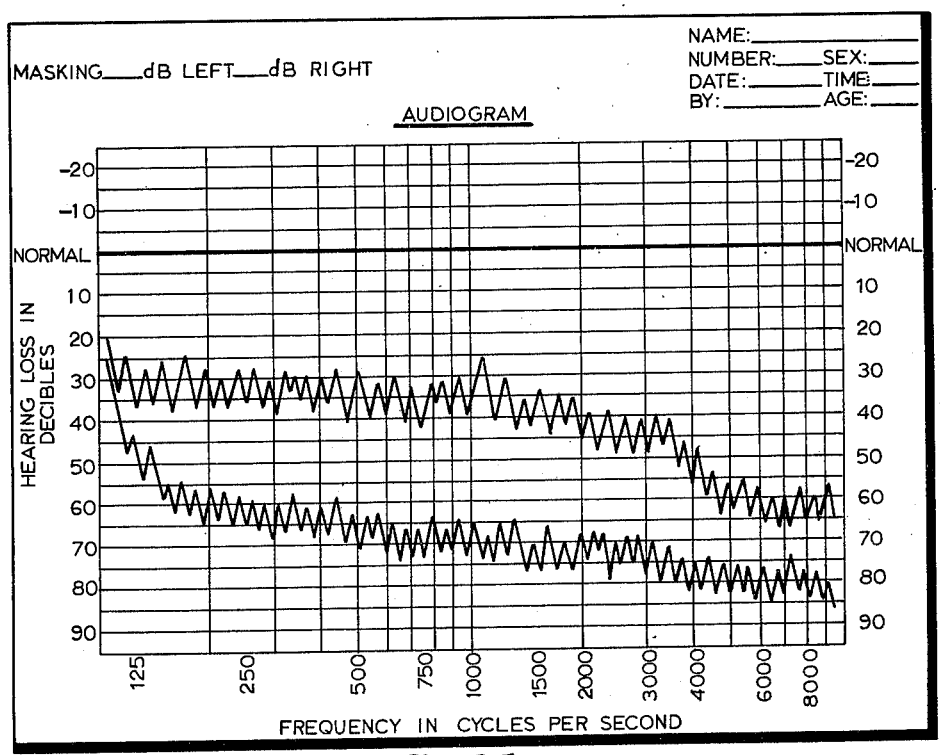
FIG. 22 (TYPE IV BEKESY AUDIOGRAM)

PORTABLE BEKESY TYPE DIAGNOSTIC AUDIOMETER

BACKGROUND OF THE INVENTION

1. Field of the Invention

The present invention relates to audiological testing devices and specifically to an automatic diagnostic audiometer adapted to test the hearing of an individual wherein the individual being tested regulates whether the sound intensity to which he is being exposed automatically increases into or decreases from his range of audibility.

2. Description of the Prior Art

Automatic audiometry can be defined as a self-administered hearing test. More accurately, it is a hearing test performed by an instrument designed to present automatically changing tone frequencies while the degree of sound intensity of the signal is controlled by the examinee, the entire test sequence being simultaneously recorded on a synchronously coupled automatic recorder. The earliest known automatic audiometer was developed by Bekesy and improved by Reger. Reference is made to George von Bekesy, "A New Audiometer", *Acta Otolaryngologica*, Vol. 35 (1947), pages 411–422, and Scott N. Reger, "A Clinical and Research Version of the Bekesy Audiometer", *Laryngoscope*, Vol. 62 (December, 1952), pages 1333–1351. In accordance with the teachings of Bekesy, a motor driven pure tone oscillator is swept from the lowest to the highest test frequency in a continuous progression. In another mode of operation termed the "reverse Bekesy test", the oscillator is adapted to be swept from the highest to the lowest test frequency, likewise in a continuous progression. An attenuator or level control comprising, for example, a potentiometer, is driven by a reversible electric motor, the direction of which is determined by a push button switch operated by the examinee. The examinee is instructed to push the button as long as he hears the signal and keep it depressed until it fades from audibility, then to release it immediately. The tone will then fade into audibility again and the earlier process is repeated. The examinee then listens for the test tones through appropriate earphones. Upon his hearing the test tone and depressing the button, the motor causes the attenuator to decrease the intensity of the output through the earphones; when the button is released, the motor reverses itself and starts an increase in the intensity of the output signal. An ink writing recorder usually coupled by gears, chains, and the like, to the attenuating and frequency sweeping mechanisms of the audiometer, traces out an audiogram representing the examinee responses to the various test tones presented. Note, for example, U.S. Pat. No. 2,653,384 which teaches an apparatus embodying an automatic audiometer according to Bekesy, synchronously coupled to a drum recording mechanism. As a further reference, a representative automatic audiometer based on the above teachings of Bekesy was manufactured by Grason Stadler, Inc., of West Concord, Massachusetts, and was designated, during the period in which it was at one time manufactured, as Model E-800. This particular audiometer has found primary application in clinical diagnostic work and research.

An offshoot of the Bekesy clinical and research audiometer is the automatic screening audiometer widely used in industrial and military testing programs. The major difference between the Bekesy automatic and the screening automatic audiometers is that the latter uses discrete frequencies, usually 500, 1000, 2000, 3000, 4000, and 6000 Hertz, instead of the continuous frequency sweeping taught by Bekesy. The automatic screening audiometer in operation dweels on each of the above frequencies for approximately 30 seconds, automatically switches to the opposite ear and repeats each of the frequencies. During the 30 second test interval the examinee uses the manual pushbutton to trace his hearing threshold on a suitable chart or drum recording instrument. This type of audiometer is commonly referred to as the Rudmose Recording Audiometer. Reference is made to R. F. McMurray and Wayne Rudmose, "An Automatic Audiometer for Industrial Medicine", *Noise Control*, Vol. 2 (January, 1956), pages 33–36. A representative example of this type of audiometer is sold by Tracor Electronics Company of Austin, Texas, and is designated Model ARJ-4. Several other firms have also introduced new industrial automatic recording audiometers; for example, Medical Measurement Instruments, Inc., Model 1000 and Grason Stadler, Inc., Model 1703. Reference is also made to U.S. Pat. No. 2,781,416 which teaches an automatic screening audiometer. Other prior art to be considered includes U.S. Pat. Nos. 2,537,911; 2,781,416; 3,007,002; and 3,392,241.

While the above mentioned prior art has in every case constituted significant advances in the field of audiology, those skilled in the art have noted certain deficiencies over the years. The most commonly noted deficiency is the extraneous noise generated by the use of motors, gear drives, chain links, stepping switches, solenoids, and relays. Such devices are not only subject to wear and misalignment, but also are a source of acoustic noise, constituting a deterrent to the accurate determination of hearing thresholds. Additional and separate rooms of soundproof construction, costing, at present prices, approximately $100 per square foot, are usually required to contain the prior art type audiometers. Since the examinee is the operator of an automatic audiometer, however, it is desirable to have a silent audiometer capable of being left near the subject, or in any case, within the same room.

As an added disadvantage, audiometers of the prior art have employed vacuum tubes with their attentdant failures and heat emission, often have weighed in excess of 100 pounds, and have occupied considerable table or console space. While newer updated versions of audiometers are lighter due to the partial utilization of semiconductor electronic components they still require approximately the same surface area for housing. Even those audiometers employing transistor construction, however, utilize numerous relays for switching, along with other electromechanical components. All existing automatic audiometers of the prior art have varying amounts of acoustic noise when received as new before wear on gear trains or motors occur.

Even further disadvantages have been cited by those skilled in the art regarding calibration of conventional audiometers. In most cases mechanical as well as electronic calibration parameters are involved and there is present the need to align the two with respect to each other. Calibration components are furthermore typically inaccessible when the conventional audiometer is in its normal operating mode. Even when access to calibration components is possible, components are not usually adjustable and must be desoldered and exchanged for other values.

Other audiometers of the prior art have employed photocells and appropriate variable light sources or field effect transistors, to induce variance in sound attenuation without requiring the use of the conventional potentiometric attenuators, but even these electronic components have not been wholly satisfactory in that they have introduced signal distortion and nonlinearity at some degrees of attenuation. Reference may be made to "Description of the Prior Art" referred to in U.S. Pat. No. 3,793,484, entitled "Programmable Audio Level Control Useful in Audiometric Apparatus" for an elaboration of some deficiencies.

A further disadvantage of instruments of the prior art relates to the necessity of assembling a large amount of ancillary equipment in order to implement various audiometric functions considered vital for clinical diagnosis. One example of such a function is the "lengthened off time" or "LOT" test which is later discussed and which in instruments of the prior art required the use of an external electronic switch of substantial size. Another example of such a function has to do with the provision of narrow-band tracking masking noise, as later discussed, for facilitating the determination of auditory thresholds in subjects having certain kinds of hearing deficiencies. Instruments of the prior art require an external electronic filter of substantial size and an additional source of wideband noise.

The additional equipment required to implement these two functions in addition to rendering portability of the equipment impossible, and to requiring substantial installation space, are research-oriented rather than user-oriented equipment. A high level of technical skill beyond the usual knowledge of the audiometric art was frequently required for the successful operation of this equipment.

Thus, it would be desirable to unify the above functions as well as other functions considered desirable into a single user-oriented instrument of reasonable size and weight which would preferably be portable. Such an instrument could be operated without requiring unusual technical skills and could in addition be carried to the bedside of test subjects who are unable to go to a testing area.

Improvements over the prior art are found in U.S. Pat. No. 3,793,484, entitled "Programmable Audio Level Control Useful in Audiometric Apparatus"; in U.S. Pat. No. 3,808,354, entitled "Computer Controlled Method and System for Audiometric Screening"; and in U.S. Pat. No. 3,793,485, entitled "Precision Automatic Audiometer", the specifications of which should be considered as incorporated by reference. The relation between this application and the referred to patents is, in a general sense, that U.S. Pat. No. 3,793,485 discloses a discrete frequency automatic audiometer useful in audiometric screening using a level control as described in U.S. Pat. No. 3,793,484, that the present application discloses a Bekesy type clinical or diagnostic audiometer using such a level control, and that U.S. Pat. No. 3,808,354 discloses a system using, via long distance communication, e.g., telephone lines, whereby a plurality of geographically widespread audiometers of a related type are modified for control and recording by a central computer whereby a plurality of test subjects at a plurality of geographically remote test sites may be tested simultaneously. Alternately, the computing means in U.S. Pat. No. 3,808,354 may be coupled locally to the audiometer and used on single or plural subjects.

The inherent deficiencies of conventional automatic audiometers in the prior art have also generated a need for an automatic clinical or diagnostic type audiometer having improved, more accurate performance, better reliability, having no moving component parts, and which is extremely quiet in operation U.S. Pat. No. 3,793,485, entitled "Precision Automatic Audiometer" teaches a relatively quiet discrete frequency automatic audiometer for screening and what is needed is an improved diagnostic or clinical audiometer. Such an audiometer could now be placed in the immediate proximity of an examinee and by the elimination of massive conventional electro-mechanical components, could be enclosed in a small lightweight portable housing such as a portion of a chart recording instrument thereby occupying a minimum amount of table or console space. Also needed is an easily calibrated automatic clinical audiometer having pulse, sweep frequency and tone decay functions in one instrument.

SUMMARY OF THE INVENTION

The circuitry of the invention is directed to a portable audiometer adapted in one mode to provide an automatic continuously swept tone Bekesy type audiometer and in another mode to provide fixed frequencies under manual control. During a hearing test, the examinee listens to a sequence of test frequencies through suitable earphone transducers, one ear at a time, and controls the sound intensity of the various test tones being presented by a manually operable switch. A preprogrammed circuit is adapted to control the sequence of test frequencies presented by precisely regulating the amount of voltage being supplied a voltage controlled oscillator. A voltage proportional attenuator circuit receives the controlled frequency signals and is adapted to provide voltage proportional control over signal amplitude. Prior to the administration of a hearing test, the examinee is instructed to press his switch upon hearing the test tone and to release the switch when the tone is no longer heard. A solid state ramp generator controlled by this switch is adapted to supply either an increasing or decreasing control voltage to the voltage proportional solid state attenuator, whereby depression of an examinee-operated switch causes the sound intensity to which that respective examinee is being exposed to be automatically decreased by the attenuator, while release of the switch causes the sound intensity to be automatically increased. In this embodiment, the ramp voltage is characterized by a substantially linear ascending and descending wave. Except prior to the beginning of the test and for the interval immediately following the change of ears during the test, the slope of the wave is constant and preselectable by a switching means. Typical slope values used correspond to a 2.5 or 5 dB/sec., rate of attenuator progression. A tone pulsing circuit connected to the attenuator is adapted to regularly pulse the signal an examinee is hearing. The tone pulser circuit may be disabled by a switch to provide a continuous tone Bekesy test. In the preferred embodiment, tone pulsing is obtained through the action of a suitably shaped square wave voltage which is added to the linear ramp of voltage to cause the attenuator to interrupt or pulse the tone.

During the hearing test, the examinee responses are monitored by means of the control voltage emanating from the ramp generator and such control voltage is continuously recorded on a chart recording instrument provided for the individual being tested. Hearing threshold level compensation circuitry is voltage provided and acts on the voltage applied to the graphic recorder to correct for earphone deficiencies and the Fletcher-Munson curve. The extreme simplicity and smallness of the solid state circuitry utilized, allows such circuitry to be housed with the XY graphic recording instrument in a compact portable unit.

Another aspect further illustrating the portable and unified character of the audiometer of the invention is that the circuitry provides automatic narrow band noise that tracks the frequency presentation in both the automatic concept frequency mode and the manually controlled fixed frequency mode. Versatility in such a portable instrument is also found in the options for tone presentations, i.e., continuous and pulsed. Conversion of the sound pressure level to the hearing threshold level is accomplished through a diode function generator and calibration is facilitated by adjusting the diode function generator parameters. Of particular practical significance is the fact that the circuitry of the invention is essentially noise-free which means that the audiometer of the invention can be self-contained and used in its entirety within the noise-free room in which the hearing test is normally made. That is, unlike in prior art practice, the audiometer circuit components of the invention, since they are mechanically noise-free, are not required to be separated from the site of the test.

DESCRIPTION OF THE DRAWINGS

FIG. 6 is a diagram of the Y-axis signal conditioning amplifier circuit.

FIG. 7 is a diagram of the ramp voltage generator circuit.

FIG. 8 is a diagram of the tone interrupter circuit.

FIGS. 19-22 illustrate respectively Type I, Type II, Type III, and Type IV audiograms.

DESCRIPTION OF THE PREFERRED EMBODIMENT

Figure 1:
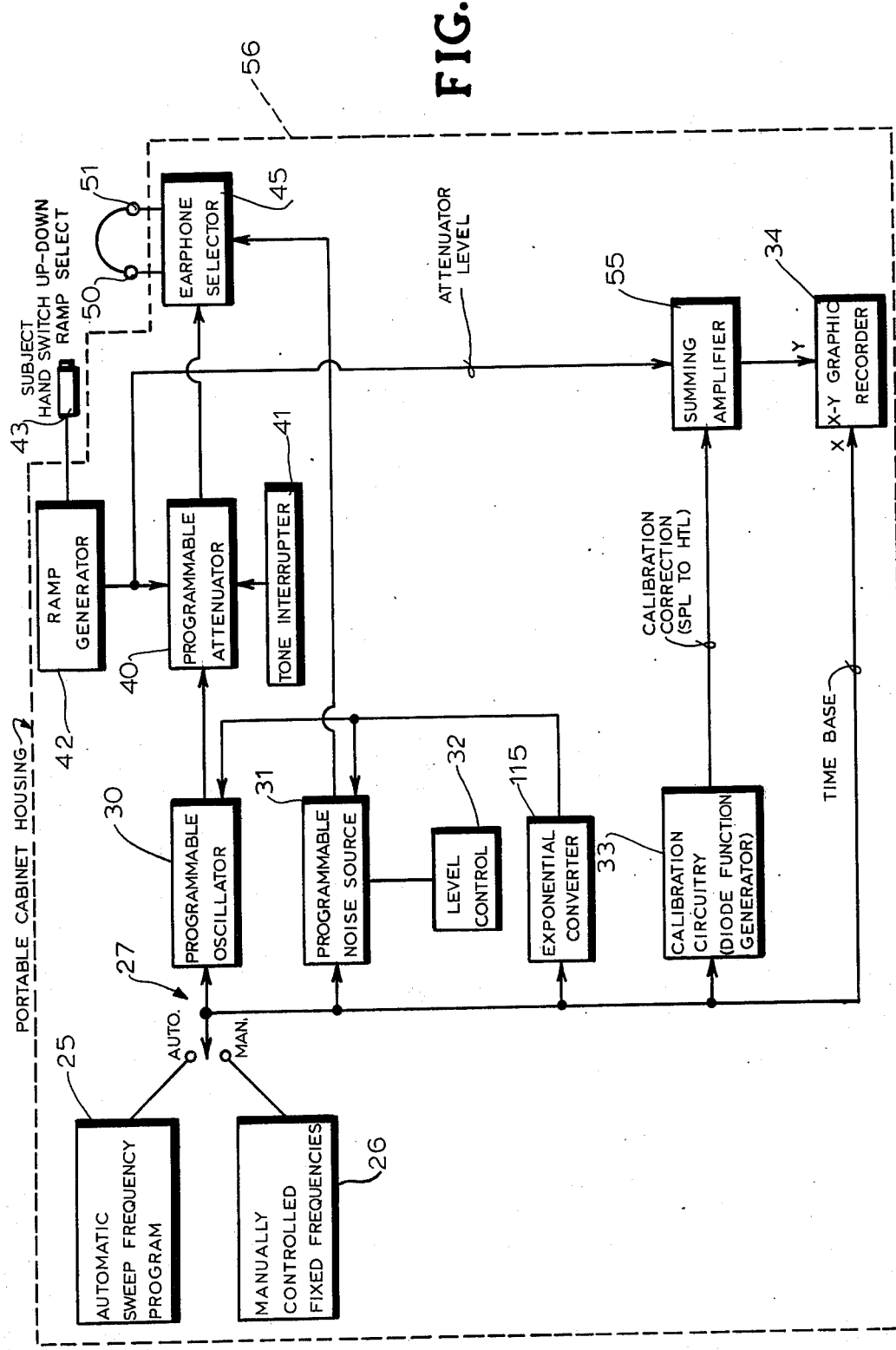
FIG. 1 is a simplified block diagram of an audiometer circuit arranged according to the invention.

In order to first gain a general appreciation of the type circuitry involved in the invention, reference is made to FIG. 1 which represents a highly simplified and generalized block diagram of the circuitry, all of which should be understood as being part of a unified, self-contained, portable device. Selection between an automatic sweep frequency program 25 and a source of manually controlled frequencies 26 is obtained through a switch 27. The selected frequencies are directed to a programmable oscillator 30, a programmed noise source 31 having a level control 32, calibration circuitry 33 (comprising a diode function generator, as later explained and as a "time base" to an X-Y graphic recorder 34.

The output of the programmable oscillator 30 is fed to a programmable attenuator 40 having a connected tone interrupter 41 and a ramp generator 42 which is controlled by the examinee's hand switch 43. An earphone selector 45 receives the outputs of both attenuator 40 and noise source 31 and feeds one output to one earphone 50 and the other to the other earphone 51 or vice versa depending on which ear is being tested and which is being masked.

To complete this general description of FIG. 1, it will be noted that the output of the calibration circuitry 33, i.e., the output of the diode function generator, provides a calibration correction, SPL (Sound Pressure Level) to HTL (Hearing Threshold Level) which is fed to a summing amplifier 55 which also receives the attenuator level as the output of the ramp generator 42. The output of summing amplifier 55 is in turn fed to the X-Y graphic recorder 34 which plots the resulting audiogram, as later explained in more detail. All of the desired circuitry, with the exception of the earphones 50, 51 and hand switch 43, is housed in a suitable cabinet 56, indicated by dashed lines in FIG. 1.

Figure 1A:
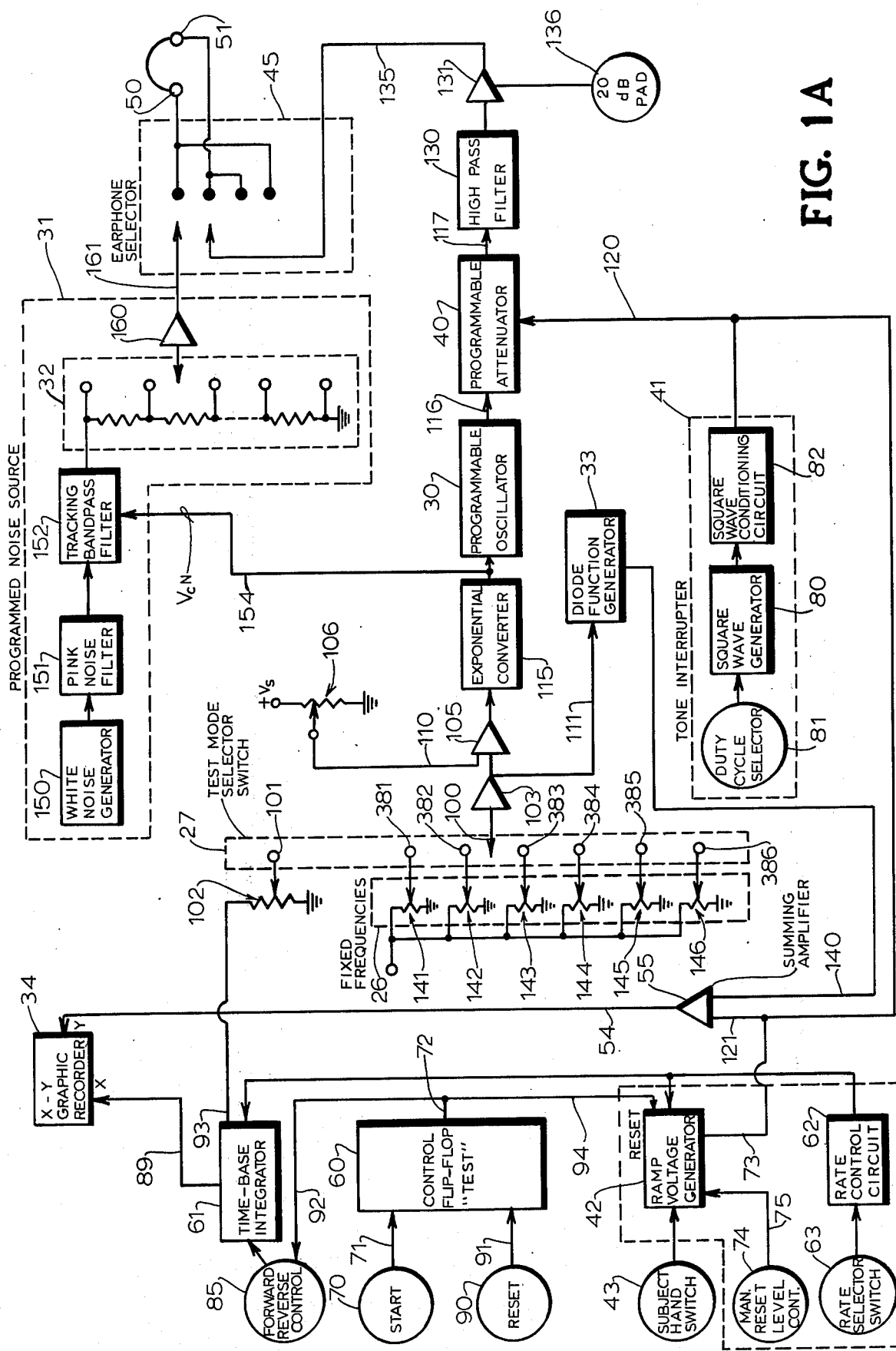
FIG. 1A is a more detailed block diagram of the FIG. 1 circuitry.

FIG. 1A presents the circuitry of FIG. 1 in somewhat more detail and FIGS. 2-12 further illustrate detailed circuitry for the various components. Where the components shown in the more detailed FIG. 1A can be seen to be readily analogous to the components illustrated in the generalized diagram of FIG. 1, the same numbers are used to designate the various elements of the circuit.

Figure 3:
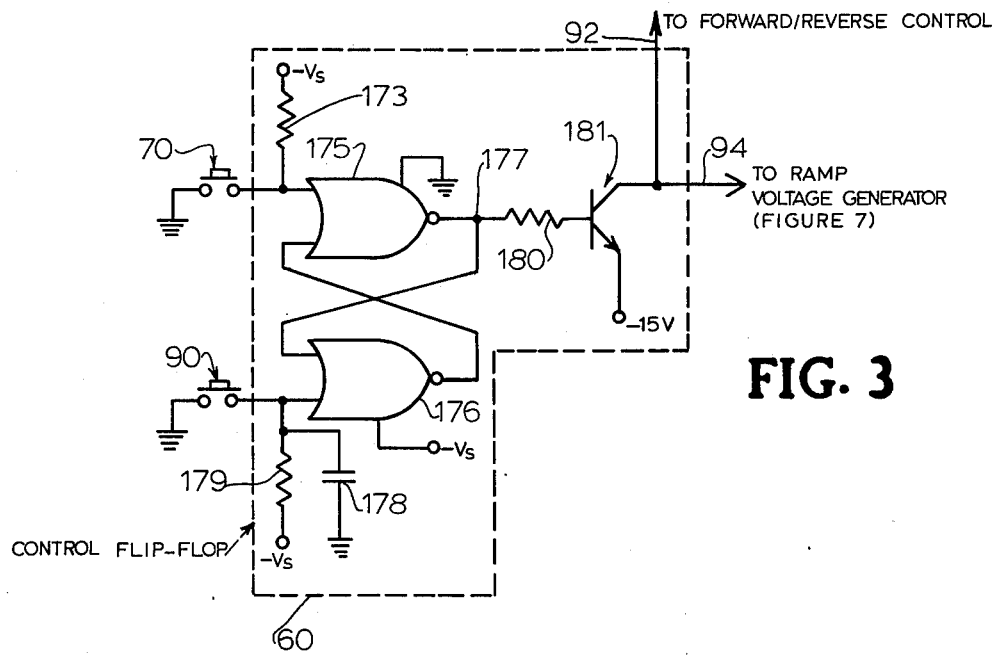
FIG. 3 is a diagram of the flip-flop circuit.

In the circuitry of FIGS. 1 and 1A, the programmable oscillator 30 is adapted to programmably generate pure tone audio signals of different selected frequencies in response to different pre-selected input voltages. The tone interruptor circuit 41 is of a type previously disclosed in U.S. Pat. No. 3,793,484 and is adapted to pulse the signals in rapid succession and at regular intervals. The programmable attenuator 40 is an analog programmable attenuator similar to the type previously disclosed in U.S. Pat. No. 3,793,484 and shown in more detail in FIG. 9. Attenuator 40 is adapted to automatically increase or decrease the amplitude of the input audio signals in a smooth progression depending on the quantity of control voltage being added to the attenuator by the ramp voltage generator, shown in more detail in FIG. 7. The examinee or subject operable switch 43 is adapted to regulate whether the ramp voltage being added to the attenuating device is caused to increase or decrease in a smooth progression. The right/left earphone selector switch 45 is adapted to regulate whether audio signals pass into the right or left earphones 50, 51 and which comprise appropriate earphone transducers for producing audible tones from input audio signals. The control flip-flop 60, indicated in FIG. 1A and which is shown in more detail in FIG. 3, provides timing control for the time-base integrator 61 and ramp voltage generator 42, thus causing a predetermined test sequence of audio signal frequencies to be generated by programmable oscillator 30. The X-Y graphic recording instrument 34 is adapted to record the ramp voltage wave which is generated during the hearing test as a linearly proportional representation of the hearing threshold level to which the individual has been exposed during the test.

Figure 2:
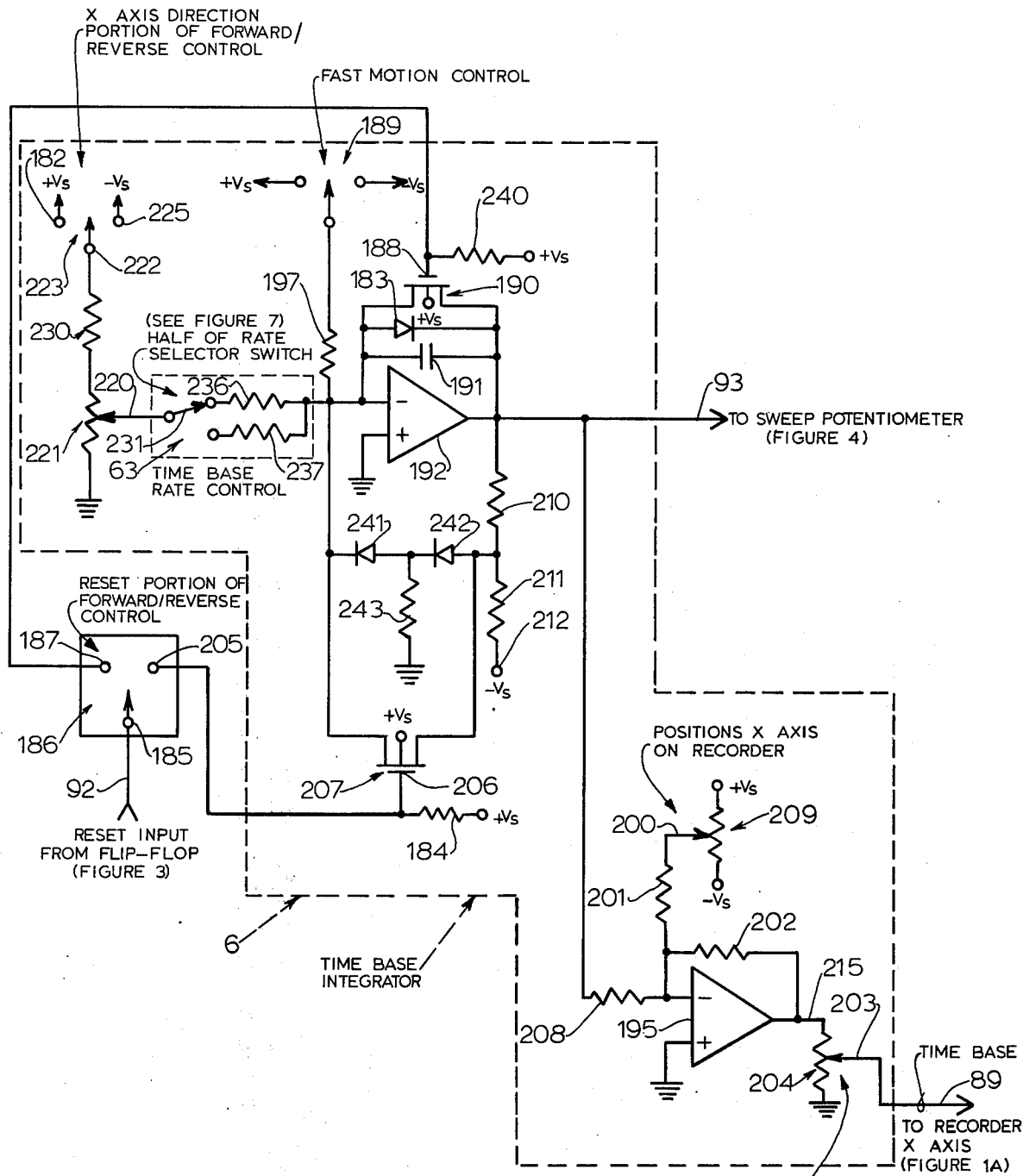
FIG. 2 is a diagram of the time base integrator circuit.
Figure 14:
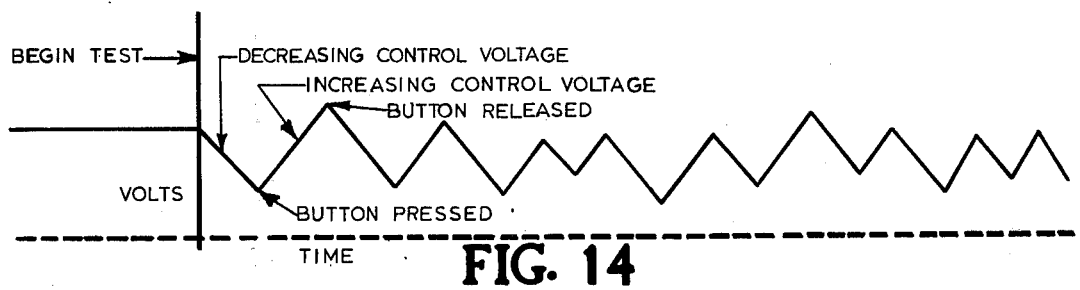
FIG. 14 is a generalized wave form of a typical envelope of ramp voltage generated during a test tone presentation.

The ramp voltage wave is characterized by a substantially linear increasing and decreasing wave as shown in FIG. 14. The slope of the wave generated 42 is made adjustable by means of a rate control circuit 62 in conjunction with a rate selector switch 63 shown in FIG. 1A. Attenuator rates normally used as 2.5 and 5 dB/sec. The time base integrator circuit 61, shown in detail in FIG. 2, is adapted to alter the integration rate to cause the test duration to be appropriate for each attenuator rate.

Figure 15:
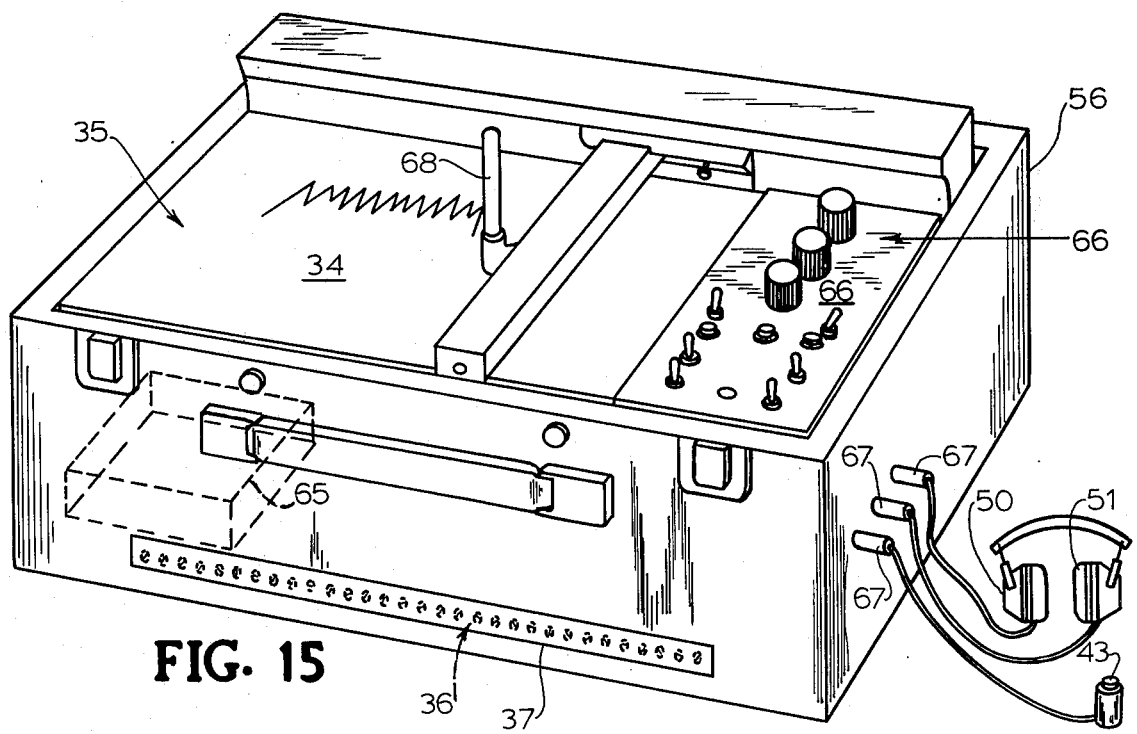
FIG. 15 is a perspective view of the complete, self-contained, portable audiometer of the invention.
Figure 16:
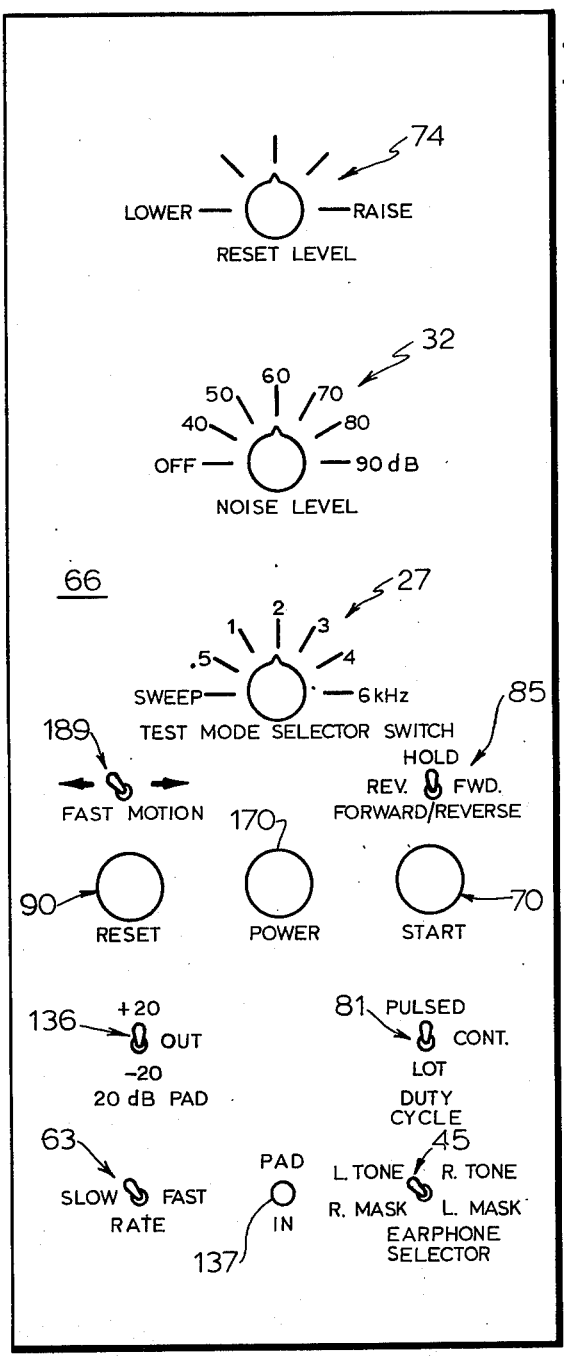
FIG. 16 is an enlarged view of the audiometer control panel.
Figure 17:
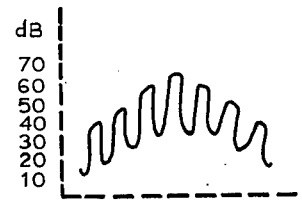
FIG. 17 is a generalized wave form representing the combination of a modified square wave and the ascending-descending linear ramp voltage of FIG. 14 being input into the attenuator.
Figure 18:
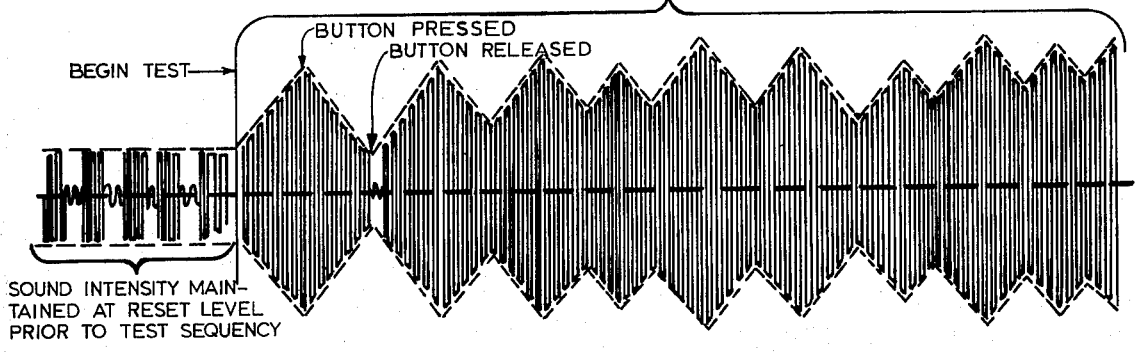
FIG. 18 is a generalized wave form showing the proportional sound pressure envelope corresponding to the application of a ramp voltage.

As further illustrated in FIG. 15, the portable cabinet is adapted to house the invention circuitry in an interior portion thereof, indicated by dashed lines 65 and is adapted to include appropriate switches and controls on a panel 66 and which are designated "Reset Level", "Noise Level", "Test Mode Selector Switch", "Fast Motion", "Forward/Reverse Control", "Reset", "Power", "Start", "20dB Pad", "Duty Cycle", "Rate", "Pad Indicator", and "Earphone Selector Switch" for manual use by a supervisor in regulating the test sequence. A more detailed view of control panel 66 is shown in FIG. 16. Earphones 50, 51 and hand switch 43 are adapted to be connected to the invention circuitry via appropriate panel jacks 67 (FIG. 15). The X-Y plotter 35 and associated mechanism 68 are mounted above the invention circuitry to the left of control panel 66.

A better understanding of the functional operation of the present invention apparatus may be had by first observing how a typical hearing test of one individual is conducted. Therefore, before further explaining the details of the circuitry and describing the operation in full, a simplified description of a typical test sequence will be described. During a hearing test, a series of auditory test tones having different selected fixed frequencies or a swept frequency sequence are presented to an examinee first through left earphone 50, then the series is repeated through right earphone 51. The examinee is instructed to depress switch 43 when he first hears the tone, a point just above his hearing threshold due to his reaction time. At the outset of the test, the first tone is adapted to automatically rise in intensity. Once the examinee hears the tone, he presses switch 43 and holds it depressed causing the intensity to automatically decrease. The tone intensity diminishes until he can no longer hear it. At this point, he has been previously instructed to release the switch, causing the test tone to begin rising in intensity again. Due to his reaction time, the point at which an examinee releases the switch is typically just below his hearing threshold. The examinee proceeds to regulate the sound intensity in a like manner for a predetermined length of time at each first test frequency. The hearing test sequence may comprise, for example, test fixed frequencies at 250, 500, 1000, 3000, 4000, 6000, and 8000 Hertz, each held for a period of time in first, then an opposite earphone, or a continuously swept frequency sequence from 250 Hz to 8 KHz or the reverse, each sweep requiring predetermined length of time, e.g., 3⅓ or 6⅔ minutes. Examinee responses in pressing or releasing switch 43 with respect to sound intensity, or corrected sound pressure level in decibels (dB), are graphed by chart recorder 34 during the hearing test. The resulting audiogram, illustrated in FIG. 20, serves as a permanent record of an examinee's hearing threshold level in each ear for each of the tone frequencies presented.

An understanding of the functional operation of the invention should also recognize the three tone presentation modes, i.e., pulsed (50% duty cycle), continuous, and LOT (200 ms on, 800 ms off) which are most often used in pairs to determine the difference in test subject response to the different tone modalities. FIGS. 19-22 show the four classical audiogram patterns obtained by comparing the subject response to successive continuous and pulsed (50% duty cycle) tone modes of swept frequency represented to the same ear. The tracings shown are like those shown in *Applied Audiometry* by O'Neill and Oyer. Dodd, Mead and Company, Inc., of New York 1966, pages 146-149. For convenience in comparison, the two tracings of each example as produced on the same audiogram form.

The Type I Beksey audiogram shown in FIG. 19, in which the tracing of the continuous and interrupted tone thresholds overlap, is associated with middle ear involvements, e.g., impairment of conduction of sound vibrations through the bones of the middle ear in otosclerosis. FIG. 20 shows the Type II Bekesy audiogram in which a small difference occurs in the continuous and pulsed tracing in the high frequencies. The continuous tracing lies below the interrupted tracing above about 1500 Hz and has a somewhat narrower envelope. This pattern is associated with cochlear involvement.

The Types III and IV Bekesy audiograms shown respectively in FIGS. 21 and 22 are characteristics of lesions of the eighth or auditory nerve. Large disparities are shown between the continuous and pulsed tracings, the continuous tone presentation tracing lying considerably below the pulsed one. The Type III audiogram (FIG. 21) shows a continuously increasing difference; the Type IV audiogram (FIG. 22) shows a relatively constant difference. By examining the relationship between the audiogram obtained with a continuous and pulsed tone presentation, the audiologist can thus, in many cases, determine the level of the auditory system at which a pathological condition exists.

A comparison between pulsed and LOT tone presentations is most often employed in the detection of an "inorganic" hearing loss, a term applied to malingering. It has been shown that a subject will have an enhanced difference in response to pulsed and LOT tone presentations when he is maintaining the tone loudness somewhat above his threshold (while simulating a hearing loss) than if the two tone presentations are being honestly maintained at the auditory threshold. The description next proceeds to the invention circuitry employed to make both the described typical test and to determine the test subject's response to the different tone modalities.

Having explained the general operation and concept of the invention circuitry and with those skilled in the art having the ability to interpret circuit diagrams such as represented by FIGS. 1-12, the description will next proceed to explaining the more detailed operation of the circuit and later, as required, mentioning those component circuit details which might otherwise not be apparent to those skilled in the art.

Referring again to FIGS. 1 and 1A, in order to initiate a "TEST" procedure, a supervisor manually presses a start button 70 which has the effect of supplying a logic 1 into input 71 of control flip-flop 60, the details of which are illustrated in FIG. 3. The resulting logic level 1 signal enters flip-flop 60 whose cross-connected COS/MOS NOR gates, seen in FIG. 3, designated "TEST", set the flip-flop and consequently cause it to output a level 0 signal at output 72. This logic 0 signal has the effect of freeing output 73 of ramp generator 42 from its reset value which is controlled by a reset level control 74 via conductor 75. Ramp generator 42 now generates a ramp having a slope of magnitude governed by a rate selector switch 63 via rate control circuit 62, and of algebraic sign governed by the position of hand switch 43.

In the previously mentioned Bekesy or sweep frequency mode, initiating the test procedure has the effect of freeing time base integrator 61 and ramp voltage generator 42 from the "reset" state. Prior to starting the test, these integrators have been held in a reset state by the logic 1 emitted by control flip-flop output 72. Tone interruption, if selected, proceeds during both reset and operate states, and also continues as part of the test procedure. In this regard, it may be noted that square wave generator 80 is adapted to emit a square wave pulse at intervals controlled by a duty cycle selector switch 81 and which pulse is transferred to square wave conditioning circuit 82, shown in FIG. 1A. A forward-/reverse control 85, seen in FIG. 1A, when in the "forward" Bekesy mode, causes time base integrator 61 to begin generating a ramp from its reset value of 0 volts to its full scale output, 10 volts, for example. It may also be noted that when forward/reverse control 85 is set in the "reverse" Bekesy mode, the ramp generated by ramp generator 42 begins at 10 volts and decreases linearly to 0 volts, for example.

Another procedure following a test is the "RESET" procedure which resets the time base integrator 61 for controlling the sequential progression test frequencies, as well as the ramp generator 42. In this procedure, a reset button 90 is pressed by the test supervisor which causes a logic 1 to be connected to digital line 91. The resulting level 1 signal enters the flip-flop circuit 60 and causes it to emit a logic 1 at output 72. This signal enters reset input 92 of time base integrator 61 causing its output 93 to output a reset value of 0 volts in the "forward" mode, or 10 volts in the "reverse" mode.

An appropriate power supply of +15, 0, −15, and +6, 0, and −6 volts D.C. may be utilized to energize the various logic and other solid state components which are being referred to in the description.

In addition to the foregoing procedure, a "RESET" instruction procedure is also provided which is adapted to cause programmable attenuator 40 to maintain a level corresponding to a sound pressure level intensity governed by the setting of manual reset level control 74 prior to the commencement of a test sequence. This is accomplished as a logic level of 1 emanating from output 72 of flip-flop 60 which enters reset input 94 of ramp generator 42 causing it to assume an output corresponding to the setting of manual reset level control 74. This reset level may be adjusted over a wide range by moving control 74. It is important to note that in the circuitry of the invention, an operational amplifier adapted for integrating purposes is utilized as ramp voltage generator 42 and is adapted to supply a ramp control voltage to programmable attenuator 40. The initial corresponding voltage level is maintained as long as a logic 1 signal is present as in the case of a "RESET" instruction. When in the case of a "TEST" instruction, a logic 0 signal is present, ramp generator 42 is released from its reset condition thereby transferring control of ramp generator 42 to examinee operated switch 43.

In the "forward" Bekesy mode of operation, during the test sequence, time base integrator 61 sweeps from 0 to 10 volts corresponding to a test frequency sweep from 250 Hz to 8 KHz, at a rate controlled by the setting of rate selector switch 63. When the full scale value of 10 volts is reached, time base integrator 61 remains in this state until reset button 90 is pressed. In the course of the test, the left ear of the test subject might be tested first. Earphone selector switch 45 will thus be in the "left" position causing the test tones to be channeled to the left ear. When the left ear test is complete, earphone selector switch 45 is manually changed to "right" channelling the test tones to the right ear for this phase of the test. In the "reverse" mode, time base integrator 61 sweeps from 10 to 0 volts corresponding to a test frequency sweep from 8 KHz to 250 Hz at a rate controlled by the setting of rate selector switch 63.

Continuing with the description, referring particularly to FIG. 1A, the linear ramp output of time base integrator 61 is applied to the X input of X–Y recorder 34 on line 89 causing it to progress linearly from left to right in the case of the "forward" Bekesy test, or the opposite in the case of the "reverse" Bekesy test. In the sweep frequency mode being discussed, test mode selector swtich 27 is connected in the "SWEEP" position, the arm 100 of switch 27 is connected to tap 101. In this mode of operation, an amount of ramp voltage output on line 93 by the time base integrator 61 is controlled by the setting of a potentiometer 102 and is applied through switch 27 to the input of a buffer amplifier 103. The output of amplifier 103 is in turn applied to one input of a summing amplifier 105 wherein it is combined with a fixed amount of voltage governed by the setting of an offset potentiometer 106 and which is applied to summing amplifier 105 via input 110. The voltage output of potentiometer 102 corresponds to a test frequency of 250 Hz, which may be the beginning point of the "forward" Bekesy test, or the end point of a "reverse" Bekesy test when in the sweep frequency mode. The output of summing amplifier 105 is thus a linear ramp offset by a small fixed voltage. An exponential converter 115 accepts this linear ramp and converts it to an exponential ramp. A suitable converter is the Analog Devices Model 755N produced by Analog Devices, Norwood, Massachusetts.

The output of exponential convertor 115 is applied to the input of the voltage programmable oscillator, e.g., Wavetek Model 120-021, which includes a sine wave converter, e.g., Wavetek Model 120-022, both available from Wavetek, San Diego, California. The output of programmable oscillator 390 is a pure size wave, the frequency of which, expressed in Hertz, is proportional to the output voltage of exponential converter 115, and which expressed in octaves in proportional to the output of time base integrator 61. As the time base integrator 61 sweeps at a constant rate during a Bekesy mode test, the sine wave produced by oscillator 30 is adapted to sweep from a lower frequency limit set by offset potentiometer 106 to an upper frequency limit, determined by potentiometer 102, with each octave of change requiring a fixed duration of time, e.g., 1 minute. A sweep from 250 Hz to 8 KHz being a change of 5 octaves would then require an interval of 5 minutes.

To continue the description, it may be noted that the sine wave output of programmable oscillator 30 is applied to the input 116 of the programmable attenuator 40 which is adapted to increase or decrease the sine wave voltage (expressed in decibels) as its output 117 in direct linear proportion to the voltage also applied to attenuator 40 through control input 120. The control voltage obtained through input 120 is derived from output 73 of ramp voltage generator 42 which is also conveyed to input 121 of summing amplifier 55. Summing amplifier 55 is adapted to combine the output of ramp voltage generator 42 with a voltage derived from diode function generator 33 as described below.

Figure 9:
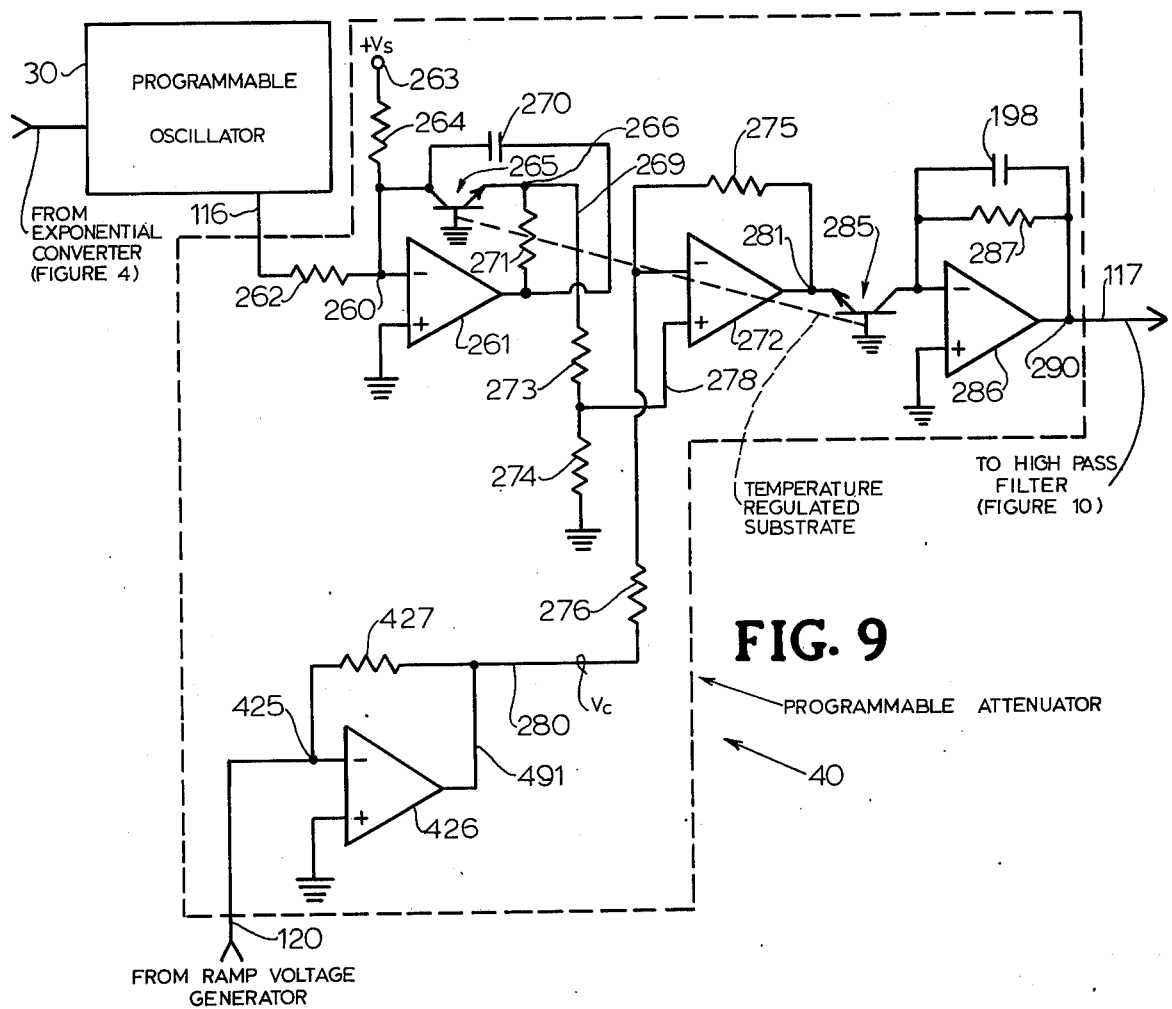
FIG. 9 is a diagram of the programmable attenuator circuit.
Figure 10:
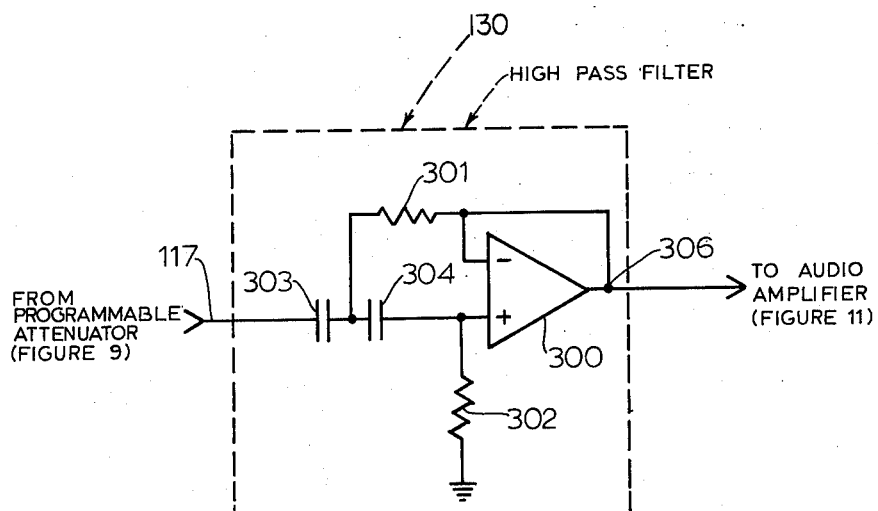
FIG. 10 is a diagram of the high pass filter circuit.

Referring now to FIG. 9 which is a schematic diagram of programmable attenuator 40 shown in FIG. 1A, amplifier 426 is adapted to accept the combination of the ramp voltage present at output 73 of ramp voltage generator 42 with the waveform derived from the tone interruptor circuit 41 shown in FIGS. 1A and 8 and which is preferably of the type previously disclosed in U.S. Pat. No. 3,793,484. This waveform has a duty cycle selected by a duty cycle selector control 81 forming part of the tone interrupter circuit 41. Duty cycles may be, for example, 100% for a continuous tone representation, 50% in one mode of pulsed tone presentation, termed "normal" and 200 milliseconds on, 800 milliseconds off (20% duty cycle) in another mode of pulsed tone presentation termed the "LOT" or "Lengthened Off Time" test. Within the tone interrupter 41, the square wave generator 80 generates a square wave of appropriate duty cycle according to the setting of the duty cycle selector switch 81. This square wave is then presented to the square wave conditioning circuit 82 which is adapted to control the rise and fall times of the square wave. The resulting square wave with controlled transition times is combined with the output ramp of ramp generator 42 at junction 422 (FIG. 7). These potentials, together with an adjustable potential obtained from potentiometer 430 applied to junction 422 through resistor 431 which adapts programmable attenuator 40 to span the proper attenuator range, are applied via line 120 (FIGS. 7 and 9) to input 425 of amplifier 426 (FIG. 9). The output of amplifier 426, which is a "pulsed ramp", is applied to conductor 280 of programmed attenuator 40 (FIG. 9) and is thus adapted to produce a pulse (or continuous) sine wave of "on" amplitude controlled by the voltage produced by ramp generator 42. This sine wave output appears at output 117 of programmable attenuator 40 and is applied to the input of a high pass filter 130. Filter 130 is adapted to remove slow voltage pulsations resulting from the action of the pulsed waveform applied to attenuator input 120 (FIG. 9) and to pass appropriate sine waves produced by attenuator 40. The output of filter 130 is applied to a power amplifier 131 which develops sine wave voltages which are transferred through line 135 at appropriate power and impedance levels for proper operation of earphones 50 and 51. Right/left earphone selector switch 45 applies this signal to the appropriate earphone as selected manually by the test supervisor. A 20 dB step attenuator 136, termed a pad control, is adapted to increase or decrease the gain of amplifier 131 by 20 dB through manual actuation of an appropriate switch position by the test supervisor. A pad indicator lamp 137 (FIG. 16) is suitably connected to be illuminated whenever the pad control is in a position other than 0 dB.

The circuitry of the invention, in addition to other functions, provides means for making corrections related both to the ear being tested and to the earphone response deficiencies. In this regard, it may be noted that the output of ramp generator 42, as previously mentioned, is applied to one input 121 of summing amplifier 55. Amplifier 55 is adapted to combine the linear ramp obtained from ramp generator 42 with a correctin voltage derived from diode function generator 33. Diode function generator 33 operates on the voltage output of amplifier 103 and produces a continuous correction voltage corresponding to the adjustments required to correct for the normal equal loudness contours of the ear plus those required to correct for frequency response deficiencies of earphones 50 and 51. Diode function generator 33 may, for example, provide a potentiometer for calibration of each of a standard set of calibration frequencies. A linear interpolation is made by diode function generator 33 between each calibration point as later discussed in more detail. A list of amplitude correction amounts at the preferred audiometric frequencies are given later in connection with a discussion of calibration and may be found in a later described table designated Table I.

The correction voltage output by diode function generator 33 is applied to input 140 of summing amplifier 55 and provides a continuous correction to the Y axis position of X-Y recorder 34, causing the Y position of the recorder pen to correspond closely to the proper hearing threshold level (HTL) corresponding to the sound pressure level (SPL) produced in the appropriate earphone 50 or 51. In the sweep mode, the X position of the recorder pen is controlled by the voltage on line 89 of time base integrator 61. The X position of the pen is thus caused, through the operation of test mode selector switch 27, amplifiers 103 and 105, exponential converter 115, and programmable oscillator 30, to correspond closely to the frequency being emitted by oscillator 30 which is being presented to the examinee subject. As the examinee maintains the tone loudness emmitted by earphone 50 or 51 near his hearing threshold through the action of hand switch 43, ramp voltage generator 42, and programmable attenuator 40, a curve, i.e., an audiogram corresponding to his hearing threshold level as a function of frequency is traced by the X-Y recorder pen as depicted in FIGS. 19-22.

In another mode of operation which may be referred to as the "fixed frequency mode", various fixed frequencies may be selected by means of test mode selector switch 27. In this mode of operation, a fixed voltage is applied to amplifier 103 and whose value is controlled by potentiometers 141-146, each corresponding to a preselected fixed frequency which may, for example, be 0.25, 0.5, 1, 2, 4, 6 and 8 KHz. In this fixed frequency mode, the ramp output of time base integrator 61 serves only to sweep the X axis of the X-Y recorder. The graph produced by the X-Y plotter becomes a plot of the hearing threshold level of the examinee as a function of time and which is sometimes referred to as a "tone decay test".

Another and sometimes critical aspect of testing a person's hearing and which is dealt with by the self-contained and portable instrument of the invention concerns the introduction of "masking" noise to meet various conditions. In this regard, it may be noted that in many cases, it is desirable to obtain the hearing threshold of a severely impaired ear when the contralateral ear of the examinee is normal. If the thresholds of the normal and impaired ear differ by more than about 50 dB at any frequency in the normal test range, the normal ear may hear the tone presented to the impaired ear because of conduction of sound through the anatomical structures of the head as well as by transmission of the tone through the air around the head. This phenomenon results in a false threshold for the impaired ear and is sometimes known as the phenomenon of the "phantom ear." This problem may be obviated by the presentation of noise in the normal ear concomitantly with the tone presented in the impaired ear. The noise presented to the normal ear causes an increase in its auditory threshold through "masking" and temporarily reduces its ability to hear the test tone being presented to the impaired ear. If properly used, masking noise permits a more accurate threshold to be obtained for the impaired ear under these circumstances.

For the purpose of masking, narrow-band noise is preferable to broadband noise, since the masking effect is more pronounced for a relatively small range of frequencies centered around a particular sine wave frequency. Noise frequencies outside this so-called "critical band" are increasingly less effective in masking the sine wave. Masking only within the critical band thus reduces the amount of noise energy that must be applied to the normal ear for proper masking. The relatively greater amount of broadband noise required may lead to temporary threshold shifts in the normal ear or to other undesired effects. Also to be noted is the fact that in the case of Bekesy sweep frequency test, the frequency of the test tone is constantly changing. For critical band masking, the noise spectrum must thus also continuously change and be maintained with its center frequency equal to the frequency of the tone presentation.

In the circuitry of the invention, masking is accomplished by a programmed noise source comprising a narrow band tracking bandpass filter, generally designated 31. Filter or noise source 31 includes a white noise generator 150 which generates broadband noise having a "white" spectrum, that is, a spectrum having a constant amount of power per unit bandwidth. The output of generator 150 is converted by a pink noise filter 151 to a "pink" spectrum having a constant amount of power per octave. "Pink" noise is used since it approximately yields an impression of constant loudness when filtered by a tracking bandpass filter of the constant percentage bandwidth type. Tracking bandpass filter 152 constitutes such a commercially available filter and is a voltage controlled, constant percentage bandwith filter whose center frequency is directly proportional to a control voltage which is applied to filter 152 through an input 154. The mentioned control voltage is derived from the output of exponential converter 115 and causes the center frequency of filter 152 to closely approximate the tone frequency generated by programmable oscillator 30. Thus, the spectrum of the noise is maintained within appropriately chosen critical band limits and which are near the frequency of the tone presentation which have been shown to be most effective in masking that tone frequency. Level control 32 consists of a step attenuator which is connected to filter 152 and which provides selection of the masking levels provided in steps, e.g., 10 dB steps. An amplifier 160 receives the noise and provides an output at 161 at appropriate power and impedance levels suitable for proper operation of earphones 50 and 51 which may, for example, be the type TDH49 earphones manufactured by Telephonics, Inc., of Huntington, Long Island, New York. The right/left earphone selector switch 45 provides proper channeling of the respective noise and test tone into contralateral earphones.

In order to more fully explain the operation of the various components, another description will be given of the circuit operation in various modes and making reference to the more specific circuit diagrams and details found in FIGS. 2-12.

At the outset, power is applied by depressing a suitably connected power switch 170 shown on control panel 66 in FIGS. 15 and 16 and which causes appropriate power supply voltage to be applied to all the active elements of the circuitry illustrated in FIG. 1A. Power now becomes available to the start button seen in FIGS. 1A and 3 and is thus available to initiate operation of the flip-flop circuit 60. Flip-flop circuit 60 includes a pair of cross-coupled NOR gates 175, 176 which may, for example, be a type CD4001AE quad NOR gate as manufactured by the Solid State Division of RCA at Somerville, New Jersey. When reset button 90 is depressed, or whenever power is applied, NOR gates 175 and 176 develop an output of a logic 1 (0 volts) at output 177 through the action of capacitor 178 and resistor 179, corresponding to a reset condition. Resistor 173 controls the input potential for NOR gate 175. The logic 1 at output 177 is applied through a suitable current limiting resistor 180 to the base of a transistor 181. Transistor 181 is thereby caused to assume an "on" condition wherein its collector assumes a potential of $-V_s$ volts which is applied to reset bus 94 and to reset a movable switch member 185 in the reset portion of forward-reverse switch 186 (FIG. 2) which comprises half of the forward-reverse control 85 shown in FIG. 1A. In the "forward" mode of operation, movable contact 185 of switch 186, as best seen in FIG. 2, is connected to contact 187 causing a potential of $-15$ volts to be applied to gate 188 of a field effect transistor (FET) 190. FET 190 may, for example, be a type HDGP 1001 manufactured by Huges Aircraft Corp. of Newport Beach, California. The potential of $-15$ volts applied to gate 188 causes FET 190 to assume a low resistance between source and drain effectively discharging capacitor 191, and causing the integrator connected amplifier 192 to output a potential of 0 volts. This potential is applied to the negative summing junction of an inverter connected amplifier 195. As best illustrated in FIG. 2, the position of contact arm 200 on the offset potentiometer 209 in conjunction with resistors 201, 202 and 208 and the position of contact arm 203 on potentiometer 204 produce an appropriate voltage $V_X$ on line 89 to the graphic X-Y recorder X-axis to cause its pen 68, shown in FIG. 15, to move to the 250 Hz position on the chart shown in FIG. 13 and which is suitably positioned on the table 35 of the recorder 34. In this mode of operation, the X-Y plotter is appropriately directed to begin a sweep from 250 Hz to 8 KHz corresponding to a forward Bekesy test. In the previously mentioned second mode of operation known as the "reverse" Bekesy mode, the movable arm 185 of switch 186, shown in FIG. 2, is adapted to connect to contact 205 causing the $-15$ volt potential present on movable arm 185 to be applied to gate 206 of FET 207 which results in the integrator connected operational amplifier 195 to output a voltage whose value is governed by resistors 210 and 211 and by a negative reference voltage at point 212. In this reverse mode of operation the potential applied to the inverter connected amplifier 195 causes it to output a voltage $V_X$ on line 89 appropriate to cause the pen mechanism 68 (FIG. 15) on recorder 34 to assume a position corresponding to 8 KHz on the chart of FIG. 13. The pen mechanism 68 of FIG. 15 is thus initialized appropriately to begin a sweep from 8 KHz to 250 Hz corresponding to a "reverse" Bekesy test.

Referring further to the time base integrator circuitry of FIG. 2, it may be noted that amplifier 192 serves to integrate potentials present at arm 220 of potentiometer 221. The movable member 222 of switch 223, shown in FIG. 2, is mechanically linked to movable member 185 of switch 186 and which switches together comprise the forward-reverse control 85, as shown in FIG. 1A and as further illustrated on the control panel 66 in FIG. 16.

In the forward Bekesy mode, as discussed above, integrator connected amplifier 192 (FIG. 2) is adapted to initially be reset to zero volts through the action of the cross-coupled gates 175 and 176 (FIG. 3) in the control flip-flop 60 of FIG. 1A and 3 and by the action of FET 190 (FIG. 2) being activated by transistor 181 (FIG. 3) when so selected by switch 186 (FIG. 2). In this same forward mode, movable member 222 of switch 223 (FIG. 2) is adapted to connect to contact 225 and to a negative reference voltage $-V_S$ designated in FIG. 2. This negative potential is conveyed via resistor 230 to potentiometer 221 which in conjunction with resistor 230 causes a controlled amount of voltage to appear at arm 220 of potentiometer 221. This voltage is, in turn, applied through switch arm 231 of rate selector switch 63 to resistor 236 in a first "fast" mode or to resistor 237 in a second slow mode, these resistor values being chosen in a ratio of 2. It may be noted that the rate selector switch 63, shown in FIG. 2, corresponds to the same rate selector switch 63 shown in the FIG. 1A. circuit and on the panel 66 in FIG. 15. In this forward mode of operation, depression of start button 70 causes cross-coupled NOR gates 175 and 176 to emit a logic 0 (−15 volts) at output 177 thereby causing transistor 181 to assume an "off" state wherein its collector assumes a voltage of +15 volts through the action of resistor 240 (FIG. 2) connected to a positive reference. This positive voltage is coupled to gate 188 of FET 190 causing it to assume a very high source to drain resistance. Such high resistance effectively eliminates the shunting effect of FET 190 across capacitor 191 allowing integrator connected amplifier 192 to integrate the negative potential present at arm 220 of potentiometer 221. The amplifier 192 is thus adapted to generate a ramp voltage beginning at 0 volts, and growing linearly in a positive direction at a rate controlled by the setting of potentiometer 221.

Potentiometer 221 may be set such that if rate selector switch 63 be set in the "fast" mode, the ramp generated at the output of amplifier 192 reaches 10 volts in approximately 3⅓ minutes corresponding to the faster mode test taught by von Bekesy. If rate selector switch 63 be set to apply voltage to resistor 237 corresponding to a second "slow" mode, the ramp generator rate is adapted to be slower by a factor of 2 than the "fast" mode, the ramp reaching 10 volts in 6⅔ minutes corresponding to the slower mode test taught by von Bekesy. In this last mentioned mode of operation, ramp generation is adapted to cease at approximately 10 volts through the current shunting action of diodes 241 and 242 and ground-connected resistor 243 (FIG. 2), acting in conjunction with resistors 210 and 211 and negative reference voltage 212.

Continuing with a discussion of the forward mode, in the Bekesy "sweep" mode of operation, accurately controlled amounts of voltage selected by potentiometer 102 (FIGS. 1A and 4) are applied to buffer amplifier 103 by reason of arm 100 of test mode selector switch 27 being connected to contact 101 corresponding to the sweep mode. For the purpose of providing the sweep frequency, the output of amplifier 103 is applied to inverter connected amplifier 105. A controllable constant offset is added to the ramp applied to amplifier 105 by means of offset potentiometer 106 connected between $+V_S$ and ground, and by means of resistors 250, 251 and 252. Capacitor 254 provides smoothing of the ramp voltage to eliminate any noise effects. The offset ramp output of amplifier 105 is applied through resistor 255 to the input of exponential converter 115, which may be a type 755N as manufactured by Analog Devices of Norwood, Massachusetts. Capacitor 256 insures stable operation of this module. The output of exponential converter 115 is an exponential ramp and is transferred to programmable oscillator 30 which may be a type 120–021 function generator acting in conjunction with a type 120–022 sine converter, both manufactured by Wavetek, Inc., of San Diego, California. These modules must be provided with appropriate distortion controls as discussed in Application Note 120-1, "Modular Generator Applications", September, 1970, by Wavetek, Inc. The output 116 of programmable oscillator 30 is a low distortion sine wave which, in the Bekesy forward sweep mode, is adapted to change gradually from a lower frequency which may be 250 Hz as controlled by ramp offsetting potentiometer 106 to a higher frequency which may be 8 KHz as controlled by potentiometer 102.

The sinusoidal output of oscillator 30 is applied to the input 116 of programmable attenuator 40 and whose detailed circuitry is seen in FIG. 9. Attenuator 40 is similar in operation to the attenuator described in U.S. Pat. No. 3,793,484 but contains certain unique circuitry and functions which render it particularly suitable for a Bekesy audiometer. With particular reference to FIG. 9, the sinusoid applied at input 116 of programmable attenuator 40 is applied to summing junction 260 of operational amplifier 261 through resistor 262. A constant positive reference potential is simultaneously applied at point 263 to summing junction 260 through resistor 264. The constant potential at point 263 and resistors 262, 264 are carefully chosen to insure proper operation of operational amplifier 261 in the logarithmic mode. Amplifier 261 is adapted through the combination of transconductor-connected transistor 265 to produce at junction 266 a logarithmic conversion of the signals present at summing juntion 260. Logarithmic conversion of electrical signals by transconductance-connected transistors is discussed in *Applications Manual For Operational Amplifiers*, published by Teletyne Philbrick of Dedham, Massachusetts. Capacitor 270 and resistor 271 insure stable operation of amplifier 261. The logarithmically converted sine wave present on line 269 is applied to input 278 of amplifier 272 which through the action of resistors 273, 274, 275 and 276 is adapted to differentially sum the signal appearing at line 269 with a control voltage signal $V_c$ presented on line 280. The signal present at output 281 is thus an algebraic sum of the logarithmically converted sine wave at output 266 and the control voltage $V_c$ presented on line 280. This algebraic sum is presented to the emitter of a logarithmic transconductor connected transistor 285. This transistor in conjunction with amplifier 286 and resistor 287 acts to produce an exponentiated version of the signal produced at output 281 of operational amplifier 272 and whose operation is made stable by capacitor 198. As discussed in U.S. Pat. No. 3,793,484, the exponentiated signal thus produced at output 290 of operational amplifier 286 contains an accurate reproduction of the sinusoid applied at input 116 of attenuator 40, having an amplitude which expressed in decibels is directly proportional to control voltage $V_c$ present on line 280.

Transistors 265 and 285 are a matched pair contained on a temperature regulated substrate as indicated in FIG. 2, and are available as an integrated circuit type NA 726 from Fairchild Semiconductor of Mountain View, California. This integrated circuit is adapted by a positive voltage source and a negative voltage source together with appropriate resistors and ground connection to maintain matched transistors 265 and 285 at the same carefully controlled constant temperature independent of ambient temperature changes, contributing to the extreme temperature stability of attenuator 40. Residual low frequency signals also produced at output 290 are effectively removed by high pass filter 130 shown in FIG. 1A and in more detail in FIG. 10. Operational amplifier 300 together with resistors 301 and 302 and capacitors 303 and 304 form a second order high pass filter having a frequency cutoff appropriately chosen to eliminate slowly changing potentials present at output 290 of amplifier 286 due to changes in control voltage $V_c$, and to pass with negligible alteration the desired sinusoidal components of the signal at output 290. The appropriately filtered signal appears at output 306 of amplifier 300.

Figure 11:
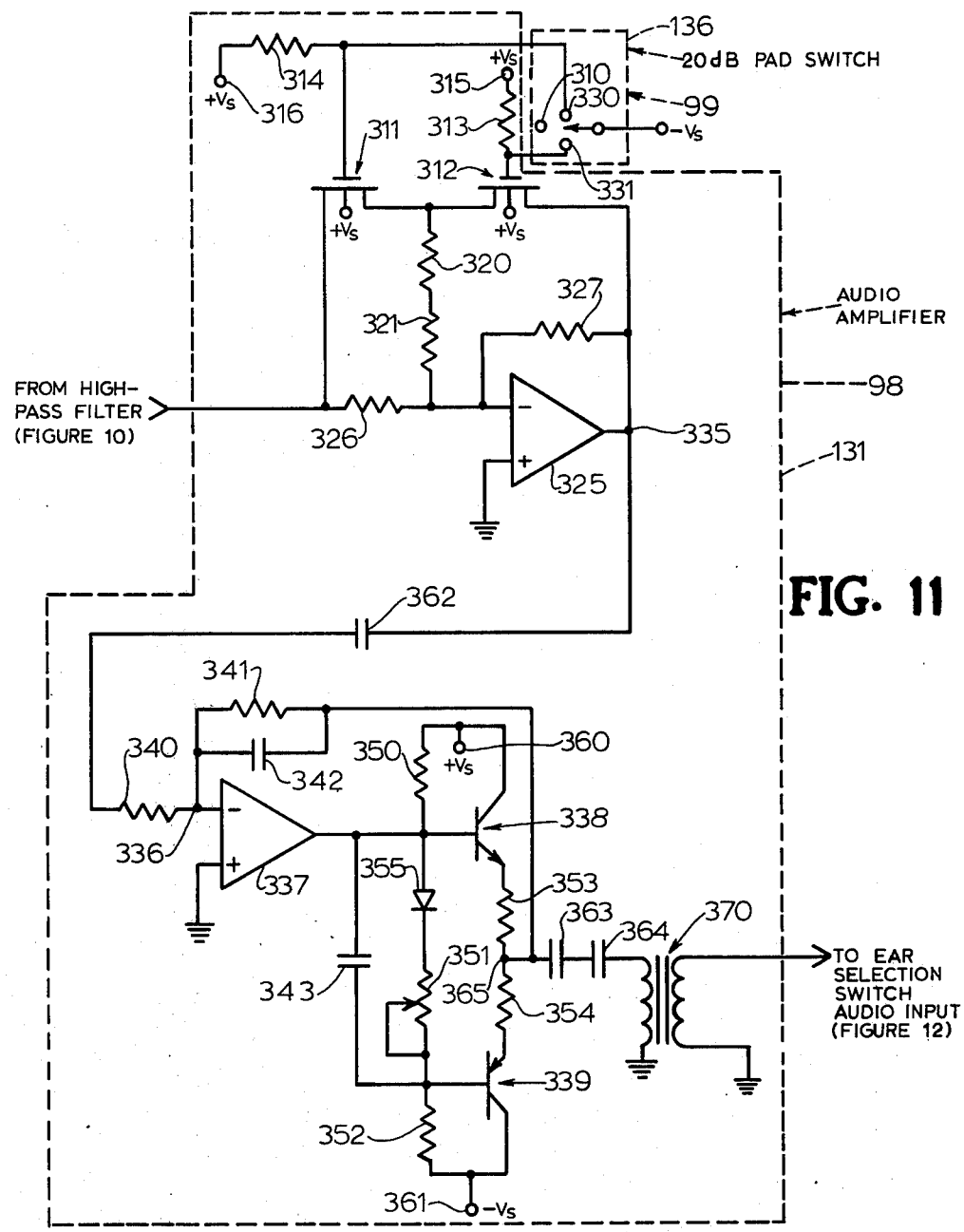
FIG. 11 is a diagram of the audio amplifier circuit.
Figure 12:
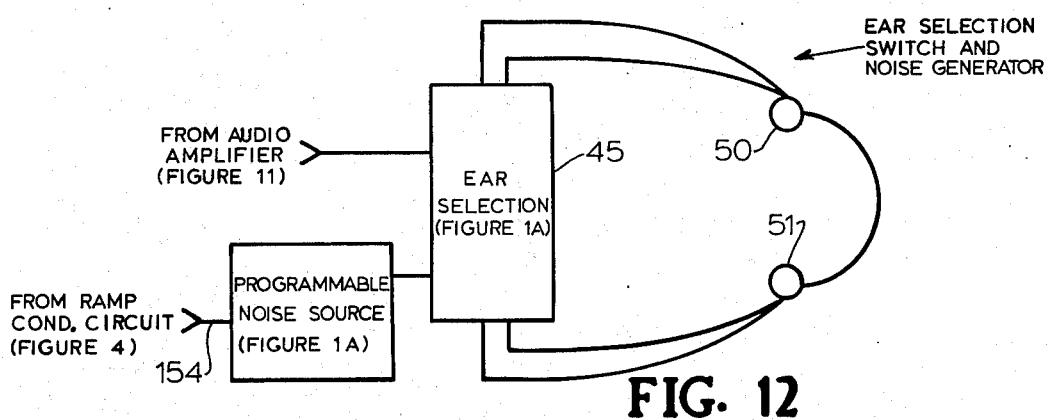
FIG. 12 is a diagram of the ear selection switch and noise generator circuit.

The output 306 of filter 130 is applied to the input of a programmable gain amplifier 131 as seen in FIG. 1A and in more detail in FIG. 11. Amplifier 131 is adapted to have a stepwise adjustable gain of −20 dB, 0 dB, or 20 dB selectably by means of pad switch 136 corresponding to the element of that number shown in FIG. 1A. In one mode of operation with the arm of switch 136 touching contact 310, the gates of field effect transistors 311 and 312 are caused through the action of resistors 313 and 314 together with positive voltage sources at points 315 and 316 to assume a positive potential, causing these FET's to assume a very high resistance from source to drain, effectively preventing series connected resistors 320 and 321 from exerting an effect upon operational amplifier 325. The gain magnitude of amplifier 325 is thus adapted through the action of resistors 326 and 327 to be minus unity, or 0 dB.

In another mode of operation, the movable member of switch 136 is adapted to touch contact 330 causing the gate of FET 311 to be driven negative. FET 311 is thus adapted to produce a very low resistance from source to drain and which effectively shunts series connected resistors 320 and 321 across resistor 326. The gain-magnitude of amplifier 325 is thus adapted in this mode to be 10 or +20 dB. FET 312 is not effective in this mode having a high source to drain resistance.

In a third mode of operation, the movable member of switch 136 is adapted to touch contact 331 thus driving the gate of FET 312 negative. FET 312 is thus adapted to produce a very low resistance from source to drain thus shunting series connected resistors 320 and 321 across resistor 327. The gain magnitude of operational amplifier 325 is thus adapted in this mode to be 0.1 or −20 dB.

The stepwise gain controlled sinusoid at output 335 of operational amplifier 325 is applied to input 336 of operational amplifier 337 which in conjunction with complementary transistors 338 and 339 is connected as a current boosting unity gain power amplifier. Resistor 340 and 341 maintain the gain at unity. Capacitor 342 insures stable operation of amplifier 337. Resistors 350, 351, 352, 353 and 354, in conjunction with diode 355 and positive and negative voltage sources at points 360 and 361, provide proper current bias for linear operation of transistors 338 and 339. This current bias is adjustable through the variable nature of resistor 351, and thermal stability is provided by diode 355. Capacitor 362 removes any direct current offsets accumulated at output 335 of amplifier 325 and capacitors 363 and 364 remove any corresponding offset at output 365 of transistors 338 and 339. Capacitor 343 provides a low impedance path for desired signals to the base of transistor 339. A transformer 370 provides appropriate impedance matching between transistors 338 and 339 and a standard TDH49 earphone.

Earphone selector switch 45 (FIG. 12) connects the output of transformer 370 alternately to a right earphone 51 or to a left earphone 50 as seen in FIG. 1A. Simultaneously, switch 45 connects the output 161 of the previously mentioned narrow bank tracking noise generator 31 to the opposite earphone providing masking or the ear contralateral to that under test as described above, as best seen in FIG. 1A. This narrow band noise, as introduced to earphone selector switch 45, is adapted to remain centered around the frequency of the test signal at all times by reason of the noise control voltage $V_cN$ applied at input 154 (indicated in FIG. 1A) and which is the same as that applied to the programmable oscillator 30 which generates the test tone frequencies. This property of the noise as introduced to earphone selector switch 45 is thus due to the linear control property of both the previously described programmable oscillator 30 and the linear control property of the noise generator 31.

In another mode of operation, commonly known as a reverse Bekesy mode, forward/reverse switch 85, shown in FIG. 16 and shown in greater detail in FIG. 2, is moved to the reverse position. As previously disclosed, in this mode of operation in a reset condition, the pen position of X-Y recorder 34 is adapted to move to the 8 KHz position seen to the right of the chart of FIG. 13. As previously described, this is accomplished through the reset portion 186 (FIG. 2) of forward/reverse control 85 (FIG. 16). In the reverse mode of operation, movable member 222 of X axis direction portion 223 (FIG. 2) of forward/reverse control 85 (FIG. 16) is moved to contact terminal 182 which is connected to a positive reference voltage. Upon entering an "operate" condition (as opposed to a "reset" condition previously described) by depression of start control 70 (FIG. 16) and through its effect on flip-flop 60 which acts through the reset half portion 186 of the forward/reverse control, FET 207 is adapted through the action of resistor 184 connected to a source of positive reference potential to assume a high source to drain resistance effectively releasing integrator amplifier 192 from the reverse reset condition previously described.

In this reverse mode of operation, a positive potential is applied to the input of integrator-connected amplifier 192 from the movable member 222 of the X axis direction portion 223 of forward/reverse control 85 (FIG. 16). This positive potential is applied through resistor 230 to potentiometer 221 which outputs a controlled portion of the potential through time base rate control 63 to the input of amplifier 192. The output of amplifier 192 is thereby caused to integrate in a linear ramp fashion from an initial voltage of +10 volts, for example, in an algebraically decreasing direction. A lower bound is imposed on this integration through the action of diode 183. This decreasing voltage causes pen 68 of X-Y plotter 34 (FIG. 15) to traverse in a controlled fashion from a rightmost position corresponding to 8 KHz to a leftmost position corresponding to 250 Hz. Simultaneously and synchronously, oscillator 30 (FIG. 1A) is adapted to generate test signals of decreasing frequency from 8 KHz to 250 Hz. Diode function generator 33 (FIG. 1A) acts continuously to maintain exact calibration as in the forward mode. All other functions proceed exactly as in the forward mode case, and an audiogram is obtained which may be referred to as a reverse Bekesy audiogram.

In either the forward or reverse mode of operation, it has been found convenient to cause the audiometer to proceed to a particular frequency within its range, much faster than occurs in the usual test mode. For this purpose, fast motion switch 189 (FIG. 16) provides through the action of a positive voltage $V_s$ and negative $-V_s$ and through the action of resistor 197 (as best illustrated in FIG. 2), a means of causing integrator-connected amplifier 192 to integrate rapidly in a direction which is controllable by the examiner. In this manner, the frequency of either the forward or reverse Bekesy mode can be caused by the examiner, to move rapidly to a particular frequency of interest, by moving fast motion control 189 (FIG. 2 and 16) in the appropriate direction. Upon release of control 189, the sweep frequency test will proceed as previously described in a direction controlled by forward/reverse control 85 and at a rate governed by the position of rate control 63 (FIG. 16).

Figure 4:
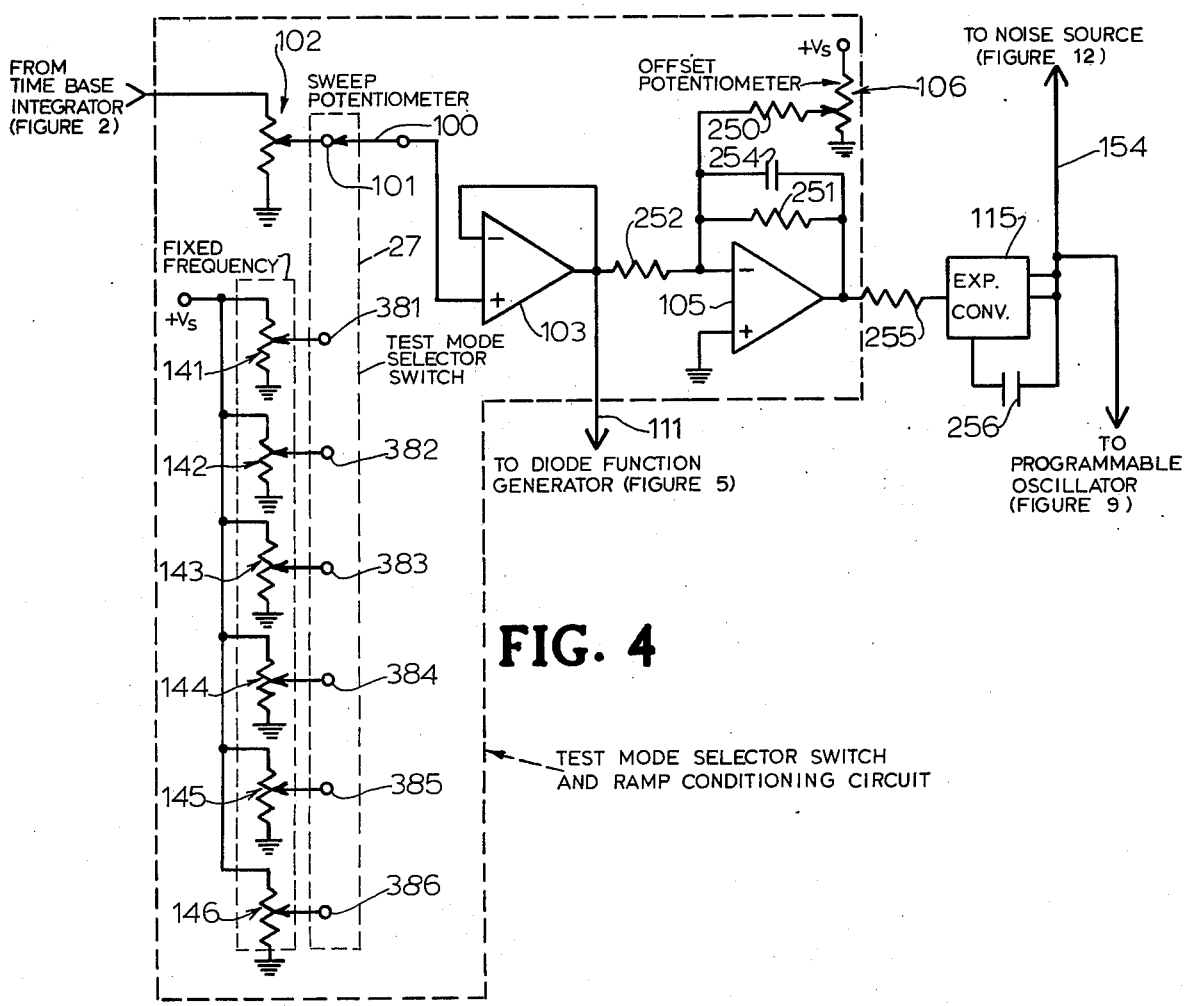
FIG. 4 is a diagram of the test made selector switch and ramp conditioning circuit.
Figure 5:
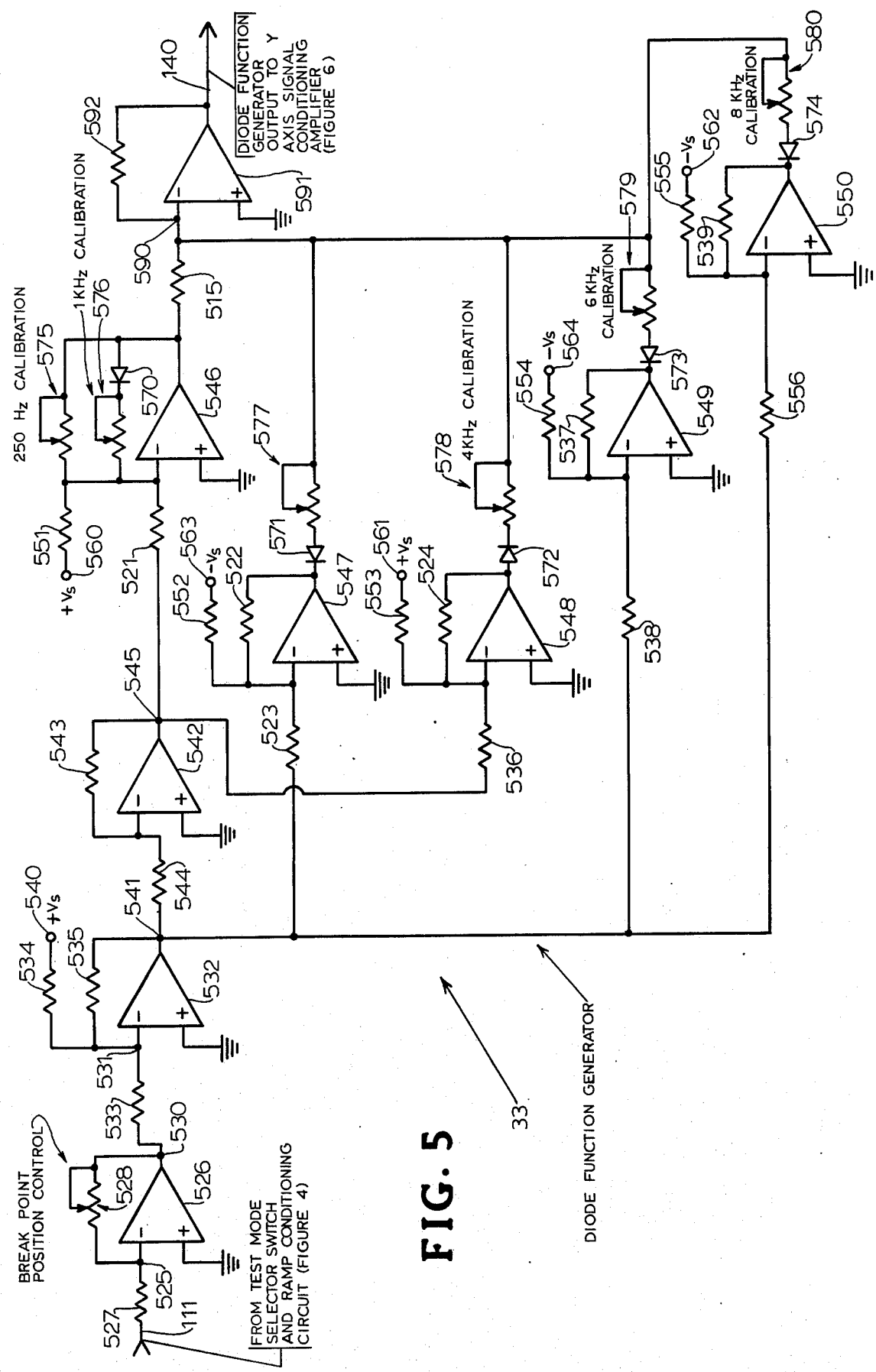
FIG. 5 is a diagram of the diode function generator circuit.

In a fixed frequency mode of operation as contrasted with the sweep frequency mode described above, a set of controlled fixed potentials illustrated in FIGS. 1A and 4 may be selected by frequency mode switch 27 by setting its movable member 100 to contacts 381, 382, 383, 384, 385 and 386. The potentials provided at these points are individually controllable by potentiometers 141, 142, 143, 144, 145 and 146, respectively, and may for example correspond to fixed test frequencies generated by programmable oscillator 30 of 500 Hz, 1 KHz, 2 KHz, 3 KHz, 4 KHz, and 6 KHz, respectively. In this mode of operation, the X-Y plotter is made to progress, customarily from left to right at either the slower or faster speed by pressing start button 70 which causes integrator connected operational amplifier 192 to integrate in a positive direction consistent with forward/reverse control 85 being in the forward position. X-Y graphic recorder 34 (FIG. 1A) is accordingly driven from left to right.

In the usual Bekesy test of either the sweep or fixed frequency type, a subject is ordinarily seated and the right and left earphones 51 and 50 (FIGS. 1, 1A and 12) are placed over the corresponding ear. In the course of the test, a sequence of auditory test tones are presented to the examinee, first through a left (or right) earphone 50, and then if applicable through a right (or left) earphone 51. At the discretion of the examiner, carefully controlled amounts of masking noise may be presented to the ear contralateral to that under test. The examinee is instructed to depress switch 43 when he first hears the tone, a point just above his hearing threshold due to his reaction time. At the outset of the test, the initial tone frequency is adapted to automatically rise in intensity. Once the examinee hears the tone he depresses switch 43 causing the tone intensity to automatically decrease. The tone intensity decreases until he can no longer hear it. At this point, he has been previously instructed to release the switch 43 causing the test tone to begin rising in intensity again. Due to his reaction time, the point at which the examinee releases the switch is typically just below his hearing threshold. The examinee proceeds to regulate the sound intensity in like manner for a predetermined length of time during either a continuously swept tone frequency progression which may extend for example from 250 Hz to 8 KHz or the reverse, or which may consist of various fixed frequencies presented in serial order as controlled by the examiner. X-Y graphic recorder 34 (FIGS. 1, 1A, and 15) meanwhile graphs a record of the sound pressure level (corrected to hearing threshold level) versus frequency (swept mode) or time (fixed frequency mode) presented to the examinee during the course of the test. The resulting audiogram (FIGS. 19-22) serves as a permanent record of the examinee's hearing threshold level in each ear tested and under the particular conditions of the test as determined by the examiner.

Continuing with the description and referring to FIG. 7, the subject's hand switch 43 is spring loaded and is thus adapted to normally contact terminal 390 connected to the $+V_s$ reference. This positive potential is conveyed to ground connected potentiometer 391, which applies a preset amount of potential to fast/slow (rate selector) switch 63, one half of which (shown in FIG. 7) is mechanically coupled to the other half shown in FIG. 2 and which together comprise the rate selector switch 63 in FIG. 1A. In the slow mode, the half of switch 63 shown in FIG. 7 causes the potential from potentiometer 391 to be applied through resistor 395 to summing junction 396 of amplifier 405. In an alternate fast mode, the half of switch 63 shown in FIG. 7 causes the potential to be applied to resistor 397 having half the value of resistor 395, and causing the potential to exert double the effect upon summing junction 490.

In the reset mode, a negative potential from the collector of transistor 181 in the control flip-flop of FIG. 3 is applied through conductor 94 to gate 399 of field effect transistor 400 of FIG. 7 causing FET 400 to produce a low source to drain resistance effectively resetting the output voltage of integrator connected amplifier 405 to a potential determined by resistor 406 and the setting of attenuator reset potentiometer 407 acting in conjunction with negative reference source 408 as seen in FIG. 7. Capacitor 410 provides the integrating function. Diode 411 imposes a negative output bound on the output voltage of amplifier 405 of approximately 0 volts. Diode 412 and resistors 413 and 414 impose an effective positive bound on the output of amplifier 405 of approximately 10 volts. In the reset condition, attenuator reset potentiometer 407 is able to control the voltage at output 415 of amplifier 405 over the full unbounded range. Ground connected potentiometer 420 applies controlled amounts of this potential through resistor 421 to junction 422 which is connected to summing junction 425 of amplifier 426 as shown in FIG. 9. Amplifier 426 in conjunction with resistor 427 produces the control voltage $V_c$ (FIG. 9) applied on line 280 of programmable attenuator 40. Proper adjustment of potentiometer 420 (FIG. 7) allows attenuator 40 to be controlled over its full range of attenuation in the reset mode by adjustment of attenuator reset control potentiometer 407 (FIG. 7). Potentiometer 430 (FIG. 7) connected between $+V_s$ and $-V_s$ references acting in conjunction with resistor 431 connected to junction 422 provides adjustment of the attenuation of attenuator 40 when the voltage at output 415 of amplifier 405 is zero volts.

The tone interrupter circuit 41 (FIGS. 1, 1A and 8) is adapted to supply an appropriately shaped pulsatile voltage to attenuator 40, causing attenuator 40 to regularly and smoothly interrupt the sinusoidal signal present at its output resulting in pulsed tone presentation to the examinee. In the pulsed mode of tone presentation integrated timer circuit 440 available from Signetics, Inc., of Sunnyvale, California, as type NE555 is caused to generate a square wave signal at its output 441. This signal is applied through resistor 442 to the base of transistor 443 which through appropriate bias resistor 444 connected to $-V_s$, and through the action of resistor 445 connected to $-V_s$ causes a square wave of appropriate amplitude to be applied to input 446 of amplifier 447 through resistor 448. This amplifier through the action of capacitor 449, zener diode 450, and positive reference connected resistor 451 is adapted to modify the rise and fall time of the square wave in a manner which eliminates any tendency for clicks or other sounds to be generated by attenuator 40 due to excessively rapid onset or extinction of the tone during pulse transitions. Resistor 460 and capacitor 461 (FIG. 8) provide further smoothing of the square wave which is then applied to junction 422 (FIG. 7) through resistor 462. The modified square wave then enters amplifier 426 (FIG. 9) and is therein combined with other attenuator control signals previously discussed and emerges as a pulsatile component of attenuator control voltage $V_c$ at line 280.

The duty cycle of the square wave determines the ratio of on to off time of the test tone and is controlled by the examinee through the action of duty cycle switch 81, FIGS. 1A and 8. In one pulsatile mode, the movable element 470 of switch 81 is adapted to touch contact 471 connected to the positive reference source. In this pulsatile mode the positive reference voltage is applied through diode 472 and is adapted to charge capacitor 473 through resistors 474 and 475. In this pulsatile mode, capacitor 473 and resistors 474 and 475 may be chosen to provide a duty cycle of 50% and a pulse rate of 2.5 per second, for example.

In an alternate pulsatile mode, the movable member of duty cycle switch 81 is adapted to touch contact 476, thus applying the positive reference voltage through resistor 477 through diode 472 and resistors 474 and 475 to capacitor 473, effectively changing the duty cycle of 20% for example, corresponding to an on time of 200 milliseconds and an off time of 800 milliseconds. This pulsatile mode is commonly referred to as the "lengthened off time" test or the LOT test, and is a proposed test for the detection of malingerers described by Karl W. Hattler in an article entitled "The Type V Bekesy Pattern: The Effects Of Loudness Memory" in the Journal of Speech and Hearing Research, Vol. 11, pages 567-575, 1968.

In a third mode of tone presentation referred to as the continuous mode, the movable member 470 of duty cycle control switch 81 is adapted to touch terminal 480, effectively applying the negative reference voltage to it. This negative causes diode 481 to conduct, drawing current out of the base of transistor 443 causing it to assume a continuously on state, allowing capacitor 449 of operational amplifier 447 to charge to and to remain at its maximum negative potention of 0 volts, effectively preventing the attenuator from being pulsed, resulting in a steady continuous tone presentation. Resistor 482 biases transistor 443.

Returning to a discussion of a test presentation, to begin the test the examinee presses start button 70 which activates control flip-flop 60 which through the action of cross-coupled NOR gates 175 and 176 in conjunction with transistor 181 (FIG. 3) causes a positive potential to be applied through conductor 94 to gate 399 of FET 400 (FIG. 7). FET 400 is thereby caused to produce a high drain to source resistance, effectively releasing integrator connected amplifier 405 from the influence of attenuator reset control 407 (FIG. 7). Integrator 405 is thus placed under the control of the subject hand switch 43, which, if not depressed, applies a positive potential to summing junction 490 of amplifier 405 which causes its output 415 to integrate in a negative direction. As previously described, an amount of this voltage controlled by potentiometer 420 is applied through resistor 421 to junction 422 connected to summing junction 425 of amplifier 426 (FIG. 9), appearing at output 491 as a control voltage ramp component tending to steadily increase the amplitude of the tone output of attenuator 40, increasing the tone amplitude presented to the examinee. When the tone becomes perceptible to the examinee he depresses hand switch 43 which connects the movable member 389 of switch 43 to contact 388 (FIG. 7) applying a portion of the negative reference voltage to the input of integrator 405. The output of integrator 405 is thus adapted to change toward increasingly positive potentials and which is applied through potentiometer 420 through resistor 421 to summing junction 425 of amplifier 426 (FIG. 9) resulting in a ramp component at output 491 tending to decrease the tone amplitude output of attenuator 40, reducing the loudness of the tone presented to the examinee. When the tone loudness becomes imperceptible to the examinee he releases hand switch 43 thus beginning a new cycle of events.

The output of integrator connected amplifier 405 now continually rises and falls in ramp-like fashion as the examinee operates hand switch 43 and maintains the tone presentation loudness near his auditory threshold. These ramp-like potential changes are applied to ground connection potentiometer 495 (FIG. 6) which applies a presetable amount of these potential changes through resistor 496 to summing junction 497 of amplifier 498. These potential changes thus appear at the output 499 of amplifier 498 through the action of the resistor 501 and are applied through line 54 (FIG. 1A and 6) to the Y axis of X-Y graphic recorder 34. The Y axis of X-Y recorder 34 is thus adapted to graph the changes in sound pressure of the tone applied to the ear of the examinee, resulting in a permanent record. Potentiometer 505 connected between positive and negative references applies an adjustable potential through resistor 506 to summing junction 497 of amplifier 498 which is summed with the ramp-like changes at output 499, and provides a convenient means of adjustment of the Y axis position of recorder 34 for calibration purposes.

According to convention, the graphing of an audiogram requires a specific correction factor at each of the preferred audiometric frequencies, to convert the tone presentation sound pressure level to an equivalent hearing threshold level, and to compensate for frequency response deficiencies in the earphones. The correction factors are expressed in decibels for each of the preferred audiometric frequencies, and when appropritely applied, result in a "flat" or level audiogram when a "normal" ear, having no hearing threshold loss, is tested. In the present invention, these corrections may be applied at the preferred audiometric frequencies by means of diode function generator 33 (FIGS. 1, 1A and 5) which generates an appropriate correction voltage at each preferred audiometric frequency proportional to the correction required at each frequency for proper calibration and applied this correction to the Y axis of the X-y graphic recorder 34.

The preferred audiometric frequencies at which calibration of the present invention may be effected are, for example, 250 Hz, 500 Hz, 1 KHz, 2 KHz, 4 KHz, 6 KHz and 8 KHz. Except for 6 KHz, these frequencies bear an octave relationship with one another over a 5 octave range. The 6 KHz frequency bears an approximate half octave relationship with 4 and 8 KHz. As previously disclosed, due to the exponentiating nature of exponential converter 115, the voltages at output 111 of amplifier 103 (FIG. 4) necessary to generate each successive octave of frequency change bear a fixed constant difference. Therefore, if 0 volts at this point causes a frequency of 250 Hz to be generated, and 2 volts causes 500 Hz to be generated, then each octave above 500 Hz will require an additional 2 volts, and each half octave will require an additional volt. The calibration differences (in decibels) necessary to effect the conversion of sound pressure level to hearing threshold level together with the compensation necessary to adjust for earphone frequency response deficiencies can then be conveniently generated by means of a nonlinear diode function generator having piecewise linear segments connecting breakpoints located at each of the voltages corresponding to the preferred audiometric frequencies listed above. It has been found that breakpoints are not required at the frequency extremes of 250 Hz and 8 KHz since no calibration need be effected beyond these extremes. The preferred audiometric frequencies and corresponding voltages are given in the following table, labeled Table I, together with the corresponding sound pressure level to hearing threshold level conversion differences.

TABLE I

| Freq. KHz | Voltage | Breakpoint | Correction difference dB |
|---|---|---|---|
| 0.25 | 0 | None | 26.7 |
| 0.5 | 2 | 2 | 13.5 |
| 1 | 4 | 4 | 7.4 |
| 2 | 6 | 6 | 11.1 |
| 4 | 8 | 8 | 10.7 |
| 6 | 9 | 9 | 13.4 |
| 8 | 10 | None | 13.0 |

(The above table is based on *Acoustica*, Vol. 18, 1967, Delaney and Whittle. The correction differences are according to ANSI-TDH49.)

Diode function generator 33 provides calibration utilizing the breakpoints located at the respective voltages shown in Table I. The voltage at output 111 of amplifier 103 (FIG. 4) is applied to negative summing junction 525 of amplifier 526 which is adapted through the action of resistor 527 and potentiometer 528 to provide variable gain means for accurately adjusting the effective distance between the breakpoints of diode function generator 33 close to the differences between those voltage values given in Table I. The accurately adjusted signal voltage available at output 530 is next applied to input 531 of amplifier 532 which is adapted through the action of resistors 533, 534 and 535 and positive voltage reference 540 to provide a constant additive offset voltage effectively shifting the breakpoints of diode function generator 33 to voltages closely corresponding to those of Table I. Output 541 of this amplifier provides voltages employed in the generation of diode function generator segment slopes of one sign, e.g., positive slopes. Amplifier 542 is adapted through the action of resistors 543 and 544 to provide an accurate inversion at unity gain of the voltage at output 541 of amplifier 532 for the purpose of generating slopes of the opposite sign, e.g., negative slopes by diode function generator 33. This inverted voltage is available at output 545 of amplifier 542. Amplifiers 546, 547, 548, 549, and 550 of diode function generator 33 act in conjunction with appropriate voltage offsetting resistors 551, 552, 553, 554, and 555 and appropriate positive references voltages 560 and 561 and appropriate negative voltage sources, 562, 563, and 564 and diodes 570, 571, 572, 573 and 574 to provide nonlinear diode function breakpoints at the voltages given in column 3 of Table 1 corresponding to the frequencies given in column 1 of Table 1. Potentiometers 575, 576, 577, 578, 579, and 580 control the slopes of the breakpoint-connecting segments of diode function generator 33 corresponding respectively to calibration intervals between 250-500 Hz, 500-1 KHz, 1-2 KHz, 2-4 KHz, 4-6 KHz and 6-8 KHz. Resistors 521-524, 536-539 and 556 provide amplifier scaling.

Figure 13:
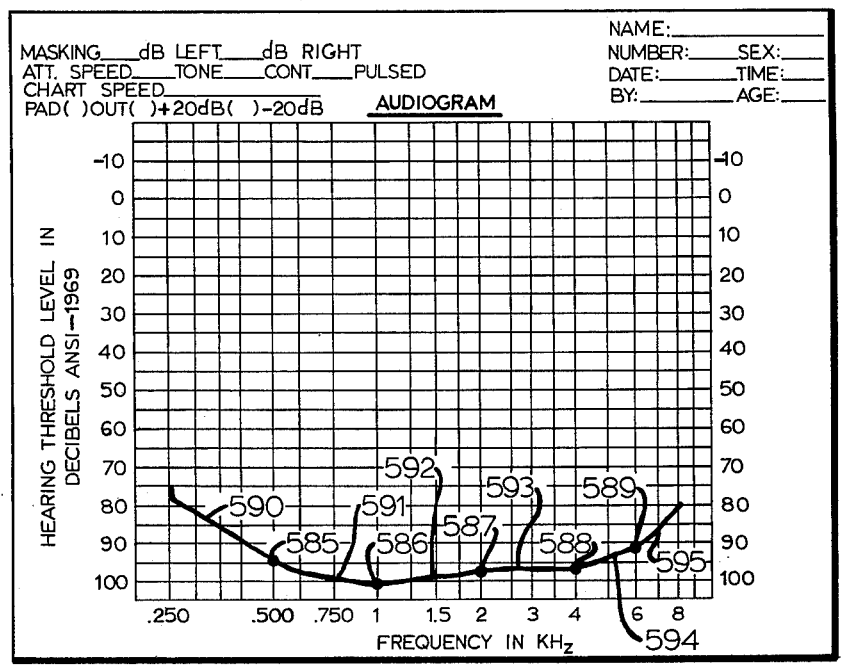
FIG. 13 is a typical curve generated by the diode function generator and which is representative of the total correction required for earphone deficiencies and sound pressure to hearing threshold level conversion.

FIG. 13 is a Bekesy audiogram form having a tracing showing breakpoints 585, 586, 587, 588, and 589 corresponding to frequencies of 500 Hz, 1 KHz, 2 KHz, 4 KHz and 6 KHz, respectively, and somewhat straight line segments 590, 591, 592, 593, 594, and 595 connecting the breakpoints and having slopes controlled respectively by calibration potentiometers 575, 576, 577, 578, 579, and 580 mentioned above. The piecewise linear curve of FIG. 13 then represents the total correction necessary as a function of frequency necessary to compensate for earphone deficiencies plus the level differences necessary to convert from sound pressure level (SPL) to hearing threshold level (HTL) relating to the curves of equal subjective loudness of the average normal ear. The curve of FIG. 13 also represents the summation of the individual slope segments generated by amplifiers 546, 547, 548, 549, and 550 acting in conjunction with diodes 570, 571, 572, 573, and 574 and slope controlling potentiometers 575, 576, 577, 578 and 579. Referring back to FIG. 5, the currents representing these slope segments are summed at summing junction 590 and are converted to equivalent voltages by amplifier 591 acting in conjunction with resistor 592. An appropriate resistor 515 is provided to couple the output of amplifier 546 to summing junction 590 of amplifier 591. This equivalent voltage is summed together with the voltage provided by the ramp voltage generator 42 at output 415 of amplifier 405 (FIG. 7) which, as previously described, is a ramp under control of the subject hand switch 43 and is employed in the regulation of the tone level presented to the subject at summing junction 497 of amplifier 498 (FIG. 6) by the application of both voltages through appropriate resistors 494 and 496 (FIG. 6). The voltage of output 499 of amplifier 498 is then a calibrated analog representation of the hearing threshold level corresponding to the second pressure level generated by appropriate earphone 50 and 51, and is thus well suited to the graphing of a hearing threshold curve by means of the X-Y graphic recorder 34.

A useful arrangement to facilitate calibration is provided by mounting all of the "trimming" potentiometers previously mentioned in a horizontal row on the front of the cabinet 56 as indicated at 36 in FIG. 15. A detachable cover 37 can be readily removed to make any specified required calibration. In this regard it may be noted that FIGS. 1A 2–8 and 11 show variable potentiometers for the various calibrations and adjustments previously discussed. Thus, all of these potentiometers can be conventionally mounted as illustrated in FIG. 15 which substantially enhances the ability to calibrate and adjust as required.

What is claimed is:

1. A diagnostic audiometer for producing an audiogram indicative of a patient's hearing threshold comprising, in combination:
    a. a set of right and left earphones;
    b. a two position patient actuated switch;
    c. programmably controllable oscillator means adapted to provide in response to application of a selected series of voltage levels in predetermined order thereto a corresponding series of continuous tone signals in corresponding order, such tone signal being of a selected audio frequency, amplitude and period of duration;
    d. a programmably controllable continuous ramp voltage source productive of a ramp voltage wave controllable as to ascending and descending direction and representing a control voltage having maximum and minimum values when moved without interruption in either direction, said ramp voltage source being connected to said two position switch and being adapted such that the direction of said ramp voltage wave may be interrupted and reversed in direction by the position of said two position switch and the magnitude of the ramp voltage wave may be regulated in coordination with desired maximum and minimum audio thresholds in said earphones;
    e. programmably controllable circuit attenuator means connected to said oscillator means to receive said tone signals and to said ramp voltages source to receive said ramp voltage wave, said attenuator means being adapted to produce therefrom a series of audio output test signals having precisely controlled gain qualties in linear proportion to said control voltage and at the selected said frequency;
    f. programmed logic controlled voltage source means connected to said oscillator means and having an output for being connected to an X-Y graphic recorder means, and being adapted to automatically provide a series of control voltages to programmably control said oscillator means in a sweep frequency mode of operation whereby upon actuation thereof said oscillator means is caused to produce said tone signals in correspondence with said control voltages and in a sweep frequency mode;
    g. a programmably controllable noise signal source connected to said logic controlled voltage source and adapted when appropriately connected to said earphones and when one ear is being tested with a particular test signal in the series to provide for the opposite ear a masking noise appropriately selected and programmed to mask said particular test signal;
    h. a manually controllable right-left earphone switch connected to both said attenuator source of audio test signals and said noise signal source of masking noise and adapted in one position to receive and direct the particular audio test signal being employed to the right ear and the corresponding masking noise being employed to the left ear and in another position to receive and direct the particular audio test signal to the left ear and the corresponding masking noise to the right ear wherein said patient hears as he manually alternates the positions of said earphone switch first in one said earphone and then in the other a programmed series of said continuous test signals in a predetermined order and repeatable sequence and as such sequence test signals proceed a corresponding sequence of said masking noises are directed to the ear not being tested and such that during the hearing of each such test signal in each respective earphone the patient is enabled to move said two position switch to a first position when said test signal is first heard and to a second position when said test signal is lost to hearing and by so positioning said two position switch said patient being able to control both the direction of said ramp voltage wave and the maximum or minimum level achieved in each direction;
    i. X-Y graphic recording means connected to said programmed logic controlled voltage source output and to said ramp voltage source and adapted to develop and record a printout for said patient in a form directly corresponding to the earphone levels heard as determined by, when and at what amplification levels the patient operates said two position switch in respect to said test signals as an indication of the patient's hearing loss.
    j. voltage responsive compensation circuit means including a diode function generator connected and adapted to provide a calibration correction voltage representing the conversion of sound pressure level to hearing threshold level and providing a compensation voltage therefor and further representing a correction for earphone frequency response deficiencies and providing an earphone deficiency correction voltage therefor; and
    k. summing amplifying circuit means connected to combine said calibration correction signal and the output of said logic controlled voltage source means and produce an output therefrom to control the Y-axis of said recording means.

2. An audiometer apparatus as claimed in claim 1 wherein said noise signal source is adapted to provide a sequence of noise signals of narrow band frequency and such narrow band frequencies are controlled by said logic controlled voltage source means to vary with the frequency of said test signals to enhance the masking thereof in the ear not being tested.

3. An audiometer as claimed in claim 1 including a tone interrupter circuit means connected to interrupt and convert said continuous tone signals into pulse form.

4. An audiometer apparatus as claimed in claim 1 wherein said oscillator means comprises a voltage controlled oscillator and said logic controlled voltage source means precisely controls the amount of voltage supplied and oscillator to control said tone signal frequency.

5. An autiometer apparatus as claimed in claim 1 including means connected to said logic controlled voltage source means for selectively presenting said tone signals in continuous, fast and slow modes of pulsed presentations.

6. An audiometer apparatus as claimed in claim 1 wherein said noise signal source includes means to regulate the level of noise produced thereby.

7. An audiometer apparatus as claimed in claim 1, including:
   a. a multi-voltage source providing a plurality of taps, each corresponding to a particular control voltage; and
   b. manual selector switching means having a first position for connecting said logic controlled voltage source means to said oscillator means for automatically providing a series of control voltages to programmably control said oscillator means in a sweep frequency mode of operation and other plural positions for selectively connecting said oscillator means to said taps for a step-by-step fixed frequency mode of operation.

8. An audiometer apparatus as claimed in claim 1 including means for precisely controlling the rate of frequency change and rate of attenuation.

9. An audiometer apparatus as claimed in claim 1 including means for controlling the direction of sweep.

10. An audiometer apparatus as claimed in claim 1 wherein said logic controlled voltage source means produces a linear control ramp wave and including circuit converter means connected between said logic controlled voltage source means and said oscillator means and adapted to convert said linear ramp wave to an exponential wave providing an octave relationship in said tone signal frequencies.

11. An audiometer apparatus as claimed in claim 1 including a cabinet and wherein said recording means is mounted on one side of said cabinet and said cabinet includes a control panel mounted on the opposite side proximate thereto, and wherein said earphone switch is mounted on said panel, said means for selectively presenting said tone signals comprises manually switchable means mounted on said panel, said means for regulating said noise level manually regulated means mounted on said panel, said manual selector switch is mounted on said panel, said means for controlling said rates of frequency change and attenuation include manually adjustable means mounted on said panel and said means for controlling said direction of sweep includes manually adjustable means mounted on said panel.

12. An audiometer apparatus as claimed in claim 1
   a. wherein said noise signal source is adapted to provide a sequence of noise signals of narrow band frequency and such narrow band frequencies are controlled by said logic controlled voltage source means to vary with the frequency of said test signals to enhance the masking thereof in the ear not being tested;
   b. including a tone interrupter circuit means connected to interrupt and convert said continuous tone signals into pulse form;
   c. wherein said oscillator means comprises a voltage controlled oscillator and said logic controlled voltage source means precisely controls the amount of voltage supplied said oscillator to control said tone signal frequency;
   d. including means connected to said logic controlled voltage source means for selectively presenting said tone signals in continuous, fast and slow modes of pulsed presentations;
   e. wherein said noise signal source includes means to regulate the level of noise produced thereby;
   f. including a multi-voltage source providing a plurality of taps, each corresponding to a particular control voltage and manual selector switching means having a first position for connecting said logic controlled voltage source means to said oscillator means for automatically providing a series of control voltages to programmably control said oscillator means in a sweep frequency mode of operation and other plural positions for selectively connecting said oscillator means to said taps for a step-by-step fixed frequency mode of operation;
   g. including means for precisely controlling the rate of frequency change and rate of attenuation;
   h. including means for controlling the direction of sweep; and
   i. wherein said logic controlled voltage source means produces a linear control ramp wave and including circuit converter means connected between said logic controlled voltage source means and said oscillator means and adapted to convert said linear ramp wave to an exponential wave providing an octave relationship in said tone signal frequencies.

13. An audiometer apparatus as claimed in claim 12 including a cabinet and wherein said recording means is mounted on one side of said cabinet and said cabinet includes a control panel mounted on the opposite side proximate thereto, and wherein said earphone switch is mounted on said panel, said means for selectively presenting said tone signals comprises manually switchable means mounted on said panel, said means for regulating said noise level includes manually regulated means mounted on said panel, said manual selector switch is mounted on said panel, said means for controlling said rates of frequency change and attenuation include manually adjustable means mounted on said panel and said means for controlling said direction of sweep include manualy adjustable means mounted on said panel.

14. An audiometer apparatus as claimed in claim 2 and including:
   a. a multi-voltage source providing a plurality of taps, each corresponding to a particular control voltage; and
   b. manual selector switching means having a first position for connecting said logic controlled voltage source means to said oscillator means for automatically providing a series of control voltages to programmably control said oscillator means in a sweep frequency mode of operation and other plural positions for selectively connecting said oscillator means to said taps for a step-by-step fixed frequency mode of operation.

15. An audiometer apparatus as claimed in claim 1 including a cabinet and including appropriate calibration and adjustment potentiometers in the circuitry thereof and being accessibly mounted for adjustment on a selected wall of said cabinet.

16. An audiometer as claimed in claim 1 including:
   a. a portable cabinet having compartments adapted to house an X-Y graphic recorder and circuitry for controlling said recorder to produce audiograms thereon;
   b. said earphones, and two position switch being adapted to being connected to circuitry within and to be used in a position proximate said cabinet; and
   c. said oscillator means, said ramp voltage source, said attenuator means, said logic controlled voltage source means, said noise signal source and said X-Y recording means being mounted in said cabinet; and said earphone switch being positioned proximate said cabinet.

* * * * *

UNITED STATES PATENT OFFICE
CERTIFICATE OF CORRECTION

Patent No. 4,038,496　　　　　　　　Dated July 26, 1977

Inventor(s) Michael D. Feezor

It is certified that error appears in the above-identified patent and that said Letters Patent are hereby corrected as shown below:

Col. 2, line 5, "dweels" should be --dwells--.

Col. 2, line 45, "attentdant" should be --attendant--.

Col. 4, line 6, a period should be inserted after "operation".

Col. 4, line 45, the comma should be deleted after "being".

Col. 5, line 36, "made" should be --mode--.

Col. 6, line 18, a parenthesis mark should be inserted after "plained".

Col. 6, line 39, "sired" should be --scribed--.

Col. 7, line 18, --by ramp generator-- should be inserted after "generated".

Col. 7, line 21, "as" should be --are--.

Col. 7, line 68, "first" should be deleted.

Col. 8, line 2, --2000,-- should be inserted after "1000,".

Col. 8, line 3, --a-- should be inserted after "in".

Col. 8, line 5, --a-- should be inserted after "requiring".

Col. 8, line 23, "represented" should be --presented--.

Col. 8, line 25, the period after "Oyer" should be a comma.

UNITED STATES PATENT OFFICE
CERTIFICATE OF CORRECTION

Patent No. 4,038,496  Dated July 26, 1977

Inventor(s) Michael D. Feezor

It is certified that error appears in the above-identified patent and that said Letters Patent are hereby corrected as shown below:

Col. 8, line 27, "as" should be --are--.

Col. 10, line 62, "390" should be --30--.

Col. 10, line 62, "size" should be --sine--.

Col. 10, line 65, second appearance of "in" should be --is--.

Col. 11, line 30, "repre-" should be --pre- --.

Col. 11, line 51, "programmed" should be --programmable--.

Col. 11, line 52, "pulse" should be --pulsed--.

Col. 12, line 13, "correctin" should be --correction--.

Col. 12, line 45, "emmitted" should be --emitted--.

Col. 13, line 54, "bandwith" should be --bandwidth--.

Col. 14, line 17, "voltage" should be --voltages--.

Col. 14, line 44, "Huges" should be --Hughes--.

Col. 15, line 38, the period after "FIG. 1A" should be deleted.

Col. 16, line 56, "juntion" should be --junction--.

Col. 18, line 7, "resistor" should be --resistors--.

Col. 18, line 28, "bank" should be --band--.

Col. 18, line 30, "or" should be --of--.

UNITED STATES PATENT OFFICE
CERTIFICATE OF CORRECTION

Patent No. 4,038,496          Dated July 26, 1977

Inventor(s) Michael D. Feezor

It is certified that error appears in the above-identified patent and that said Letters Patent are hereby corrected as shown below:

Col. 19, line 27, --voltage-- should be inserted after "negative".

Col. 21, line 7, "tojunction" should be --to junction--.

Col. 21, line 56, "of" should be --to--.

Col. 22, line 2, --potential-- should be inserted after "negative".

Col. 22, line 6, "potention" should be --potential--.

Col. 23, line 6, "appropritely" should be --appropriately--.

Col. 23, line 15, "applied" should be --applies--.

Col. 23, line 16, "y" should be --Y--.

Col. 24, line 68, the first appearance of "of" should be --at--.

Col. 25, line 48, "voltages" should be --voltage--.

Col. 26, line 37, the period should be a semicolon.

Col. 26, line 67, "and" should be --said--.

Col. 27, line 1, "autiometer" should be --audiometer--.

UNITED STATES PATENT OFFICE
CERTIFICATE OF CORRECTION

Patent No. 4,038,496   Dated July 26, 1977

Inventor(s) Michael D. Feezor

It is certified that error appears in the above-identified patent and that said Letters Patent are hereby corrected as shown below:

Col. 27, line 43, --includes-- should be inserted after "level".

Col. 27, line 49, a colon should be inserted after "claim 1".

Col. 28, line 36, "manualy" should be --manually--.

Signed and Sealed this

Fourteenth Day of February 1978

[SEAL]

Attest:

RUTH C. MASON
Attesting Officer

LUTRELLE F. PARKER
Acting Commissioner of Patents and Trademarks